United States Patent
Gottschalk et al.

(10) Patent No.: US 11,649,284 B2
(45) Date of Patent: May 16, 2023

(54) CANCER GENE THERAPY TARGETING CD47

(71) Applicant: Baylor College of Medicine, Houston, TX (US)

(72) Inventors: Stephen M. G. Gottschalk, Houston, TX (US); Felicia Cao, Houston, TX (US)

(73) Assignee: Baylor College of Medicine, Houston, TX (US)

(*) Notice: Subject to any disclaimer, the term of this patent is extended or adjusted under 35 U.S.C. 154(b) by 389 days.

(21) Appl. No.: 16/094,416

(22) PCT Filed: Apr. 18, 2017

(86) PCT No.: PCT/US2017/028050
§ 371 (c)(1),
(2) Date: Oct. 17, 2018

(87) PCT Pub. No.: WO2017/184553
PCT Pub. Date: Oct. 26, 2017

(65) Prior Publication Data
US 2019/0119379 A1    Apr. 25, 2019

Related U.S. Application Data

(60) Provisional application No. 62/323,926, filed on Apr. 18, 2016.

(51) Int. Cl.
| | | |
|---|---|---|
| A61P 35/00 | (2006.01) |
| C07K 16/28 | (2006.01) |
| C07K 14/705 | (2006.01) |
| A61K 39/395 | (2006.01) |
| A61K 45/06 | (2006.01) |
| A61K 48/00 | (2006.01) |
| A61K 38/00 | (2006.01) |
| A61K 39/00 | (2006.01) |

(52) U.S. Cl.
CPC .... *C07K 16/2803* (2013.01); *A61K 39/39558* (2013.01); *A61K 45/06* (2013.01); *A61K 48/005* (2013.01); *A61P 35/00* (2018.01); *C07K 14/705* (2013.01); *C07K 14/70596* (2013.01); *C07K 16/283* (2013.01); *A61K 38/00* (2013.01); *A61K 2039/505* (2013.01); *C07K 2317/622* (2013.01); *C07K 2319/30* (2013.01); *Y02A 50/30* (2018.01)

(58) Field of Classification Search
CPC ... C07K 16/2803; C07K 16/283; A61P 35/00; A61K 39/39558; A61K 45/06; A61K 48/005; A61K 2039/505
See application file for complete search history.

(56) References Cited

U.S. PATENT DOCUMENTS

| | | | |
|---|---|---|---|
| 5,011,912 A | 4/1991 | Hopp et al. | |
| 5,837,243 A * | 11/1998 | Deo | C07K 14/485 424/136.1 |
| 2007/0071745 A1 | 3/2007 | Umana et al. | |
| 2008/0131431 A1* | 6/2008 | Smith | C07K 14/70596 424/134.1 |
| 2013/0189253 A1 | 7/2013 | Danska et al. | |
| 2015/0071905 A1 | 3/2015 | Ring et al. | |
| 2016/0177276 A1* | 6/2016 | Lo | C07K 14/70596 424/134.1 |
| 2016/0186150 A1* | 6/2016 | Deming | A61K 47/6803 424/94.6 |
| 2018/0250395 A1* | 9/2018 | Pietsch | C07K 16/2896 |

FOREIGN PATENT DOCUMENTS

WO    2014/123580 A1    8/2014

OTHER PUBLICATIONS

Weiskopf et al, Science (2013) vol. 341, Issue 6141, 88-91. (Year: 2013).*
Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*

(Continued)

*Primary Examiner* — Julie Wu
*Assistant Examiner* — Cheom-Gil Cheong
(74) *Attorney, Agent, or Firm* — Norton Rose Fulbright US LLP

(57) ABSTRACT

Embodiments of the disclosure concern treatment of cancer utilizing methods and compositions that block CD47 such that tumor associated macrophages (TAMs) are not inhibited by CD47 and are able to phagocytose and kill tumor cells. In specific embodiments, the compositions and their use concern fusions of an entity that binds CD47 and an entity that binds cells having FC receptors, such as the FC receptor on TAMs. Certain embodiments concern gene therapy that produces a fusion of the ectodomain of SIRPa and the constant region of IgG4 at a localized tumor or tumor microenvironment, for example. In specific cases, gene transfer is utilized to deliver SIRPa fusion genes into a tumor and/or tumor microenvironment so that the molecules can be expressed locally to increase efficacy (given that the expression of the molecules will be highest at tumor sites) and decrease potential toxicities.

15 Claims, 11 Drawing Sheets

Specification includes a Sequence Listing.

(56) References Cited

OTHER PUBLICATIONS

Klimka et al., British Journal of Cancer, 2000, 83:252-260. (Year: 2000).*
Ward et al., Nature, 1989, 341:544-546. (Year: 1989).*

* cited by examiner

FIG. 5A
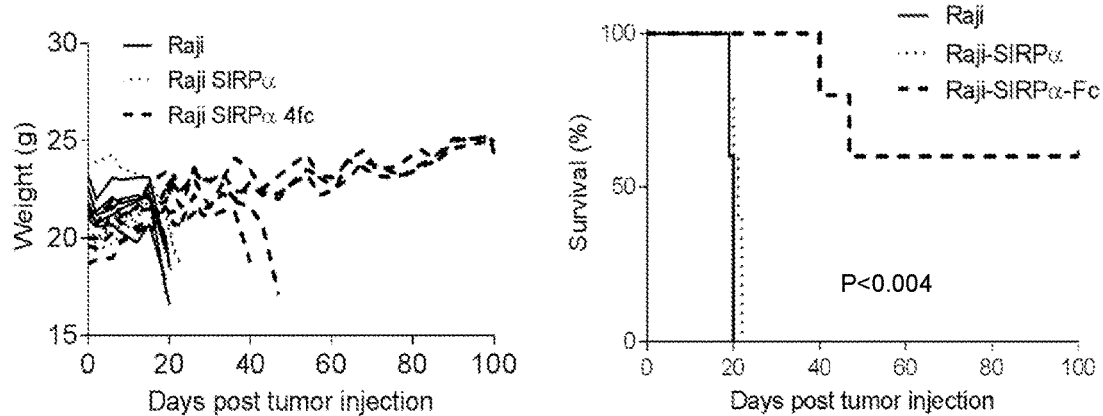
FIG. 5B
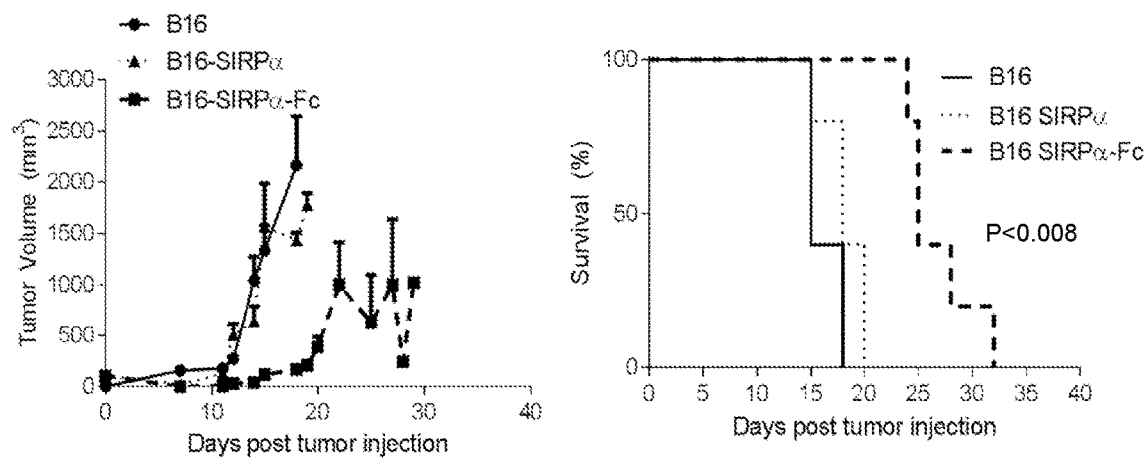
FIGS. 5A, 5B

FIG. 6A
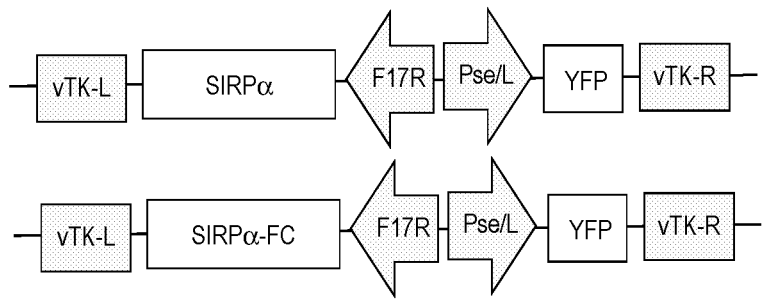
FIG. 6B
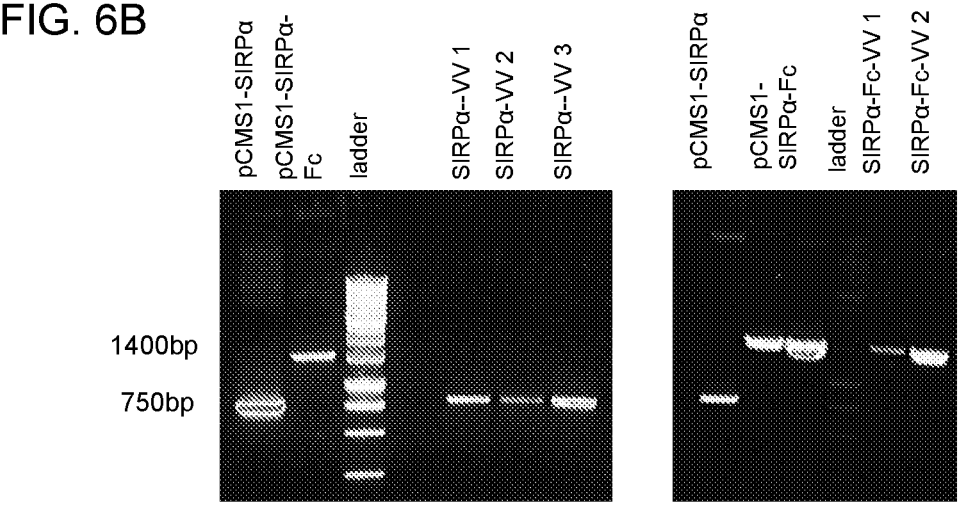
FIGS. 6A and 6B

FIGS. 8A, 8B, 8C, and 8D

OV10315 + M1 + VV sup

OV10315 + M2 + VV sup

SEQUENCE LISTING

```
<160> NUMBER OF SEQ ID NOS: 15

<210> SEQ ID NO 1
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 1

Met Asp Trp Ile Trp Arg Ile Leu Phe Leu Val Gly Ala Ala Thr Gly
1               5                   10                  15

Ala His Ser

<210> SEQ ID NO 2
<211> LENGTH: 117
<212> TYPE: PRT
<213> ORGANISM: Artificial Sequence
<220> FEATURE:
<223> OTHER INFORMATION: Synthetic Peptide

<400> SEQUENCE: 2

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
```

```
                35                  40                  45
Ile Tyr Asn Gln Lys Glu Gly His Phe Pro Arg Val Thr Thr Val Ser
 50                  55                  60

Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Thr Glu Leu Ser Val
                100                 105                 110

Arg Ala Lys Pro Ser
                115

<210> SEQ ID NO 3
<211> LENGTH: 227
<212> TYPE: PRT
<213> ORGANISM: Artificial Sequence
<220> FEATURE:
<223> OTHER INFORMATION: Synthetic Peptide

<400> SEQUENCE: 3

Ala Ala Ala Pro Pro Cys Pro Pro Cys Pro Ala Pro Glu Phe Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser Gln
                 35                  40                  45

Glu Asp Pro Glu Val Gln Phe Asn Trp Tyr Val Asp Gly Val Glu Val
 50                  55                  60

His Asn Ala Lys Thr Lys Pro Arg Glu Glu Gln Phe Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Gly Leu Pro Ser Ser Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Gln Glu Glu Met Thr Lys Asn Gln Val Ser
                130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Arg Leu Thr Val
                180                 185                 190

Asp Lys Ser Arg Trp Gln Glu Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys
225

<210> SEQ ID NO 4
<211> LENGTH: 1089
<212> TYPE: DNA
<213> ORGANISM: Artificial Sequence
<220> FEATURE:
<223> OTHER INFORMATION: Synthetic Primer
```

<400> SEQUENCE: 4

```
atggactgga tctggcggat cctgttcctc gtgggagccg ccacaggcgc ccactctgaa      60
gaggaactgc aagtgatcca gcccgacaag agcgtgctgg tggccgctgg cgaaaccgcc     120
accctgagat gtacagccac cagcctgatc cccgtgggcc ccatccagtg gtttagaggc     180
gctggccctg gcagagagct gatctacaac cagaaagagg ccacttccc cagagtgacc      240
accgtgtccg acctgaccaa gcggaacaac atggacttca gcatccggat cggcaacatc     300
acccctgccg atgccggcac ctactactgc gtgaagttcc ggaagggcag ccccgacgac     360
gtggaattca gagcggcac cgagctgagc gtgcgggcca accttctgc tgccgctcct       420
ccttgccctc catgtcctgc ccctgagttt ctgggcggac ccagcgtgtt cctgttcccc     480
ccaaagccca aggacaccct gatgatcagc cggaccccg aagtgacctg cgtggtggtg      540
gatgtgtccc aggaagatcc cgaggtgcag ttcaattggt acgtggacgg cgtggaagtg     600
cacaacgcca agaccaagcc cagagaggaa cagttcaaca gcacctaccg ggtggtgtcc     660
gtgctgaccg tgctgcacca ggactggctg aacggcaaag agtacaagtg caaggtgtcc     720
aacaagggcc tgcccagcag catcgagaaa accatcagca aggccaaggg ccagcctcgc     780
gagccccagg tgtacacact gcctccaagc caggaagaga tgaccaagaa ccaggtgtcc     840
ctgacctgtc tcgtgaaggg cttctacccc tccgatatcg ccgtggaatg ggagagcaac     900
ggccagcccg agaacaacta caagaccacc cccctgtgc tggacagcga cggctcattc      960
ttcctgtaca gcagactgac cgtggacaag agccggtggc aggaaggcaa cgtgttcagc    1020
tgcagcgtga tgcacgaggc cctgcacaac cactacaccc agaagtccct gagcctgagc    1080
cccggcaaa                                                            1089
```

<210> SEQ ID NO 5
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 5

```
Met Asp Trp Ile Trp Arg Ile Leu Phe Leu Val Gly Ala Ala Thr Gly
1               5                   10                  15

Ala His Ser
```

<210> SEQ ID NO 6
<211> LENGTH: 119
<212> TYPE: PRT
<213> ORGANISM: Artificial Sequence
<220> FEATURE:
<223> OTHER INFORMATION: Synthetic Peptide

<400> SEQUENCE: 6

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
                20                  25                  30

Val Gly Pro Ile Gln Trp Phe Arg Gly Ala Gly Pro Gly Arg Val Leu
            35                  40                  45

Ile Tyr Asn Gln Arg Gln Gly Pro Phe Pro Arg Val Thr Thr Val Ser
        50                  55                  60

Asp Thr Thr Lys Arg Asn Asn Met Asp Phe Ser Ile Arg Ile Gly Asn
```

```
                65                  70                  75                  80
Ile Thr Pro Ala Asp Ala Gly Thr Tyr Tyr Cys Ile Lys Phe Arg Lys
                    85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 7
<211> LENGTH: 227
<212> TYPE: PRT
<213> ORGANISM: Artificial Sequence
<220> FEATURE:
<223> OTHER INFORMATION: Synthetic Peptide

<400> SEQUENCE: 7

```
Ala Ala Ala Pro Pro Cys Pro Pro Cys Pro Ala Pro Glu Phe Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser Gln
        35                  40                  45

Glu Asp Pro Glu Val Gln Phe Asn Trp Tyr Val Asp Gly Val Glu Val
    50                  55                  60

His Asn Ala Lys Thr Lys Pro Arg Glu Glu Gln Phe Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Gly Leu Pro Ser Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Gln Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Arg Leu Thr Val
            180                 185                 190

Asp Lys Ser Arg Trp Gln Glu Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 8
<211> LENGTH: 1095
<212> TYPE: DNA
<213> ORGANISM: Artificial Sequence
<220> FEATURE:
<223> OTHER INFORMATION: Synthetic Primer

<400> SEQUENCE: 8

```
atggactgga tctggcggat cctgttcctc gtgggagccg ccacaggcgc ccactctgaa      60
gaggaactgc agatcatcca gcccgacaag agcgtgctgg tggccgctgg cgaaaccgcc     120
```

```
acccctgagat gtaccatcac cagcctgttc cctgtgggcc ccatccagtg gtttagaggc    180
gccggacctg gccgggtgct gatctacaat cagagacagg gcccattccc cagagtgacc    240
accgtgtccg acaccaccaa gcggaacaac atggacttca gcatccggat cggcaacatc    300 accccctgccg atgccggcac ctactactgc atcaagttcc ggaagggcag ccccgacgac    360
gtggaattca aagcggagc cggcaccgag ctgagcgtgc gggctaaacc ttctgccgcc    420
gctcctcctt gccctccatg tcctgcccct gagtttctgg gcggacccag cgtgttcctg    480
ttccccccaa agcccaagga caccctgatg atcagccgga cccccgaagt gacctgcgtg    540
gtggtggatg tgtcccagga agatcccgag gtgcagttca attggtacgt ggacggcgtg    600
gaagtgcaca acgccaagac caagcccaga gaggaacagt tcaacagcac ctaccgggtg    660
gtgtccgtgc tgaccgtgct gcaccaggac tggctgaacg gcaaagagta caagtgcaag    720
gtgtccaaca agggcctgcc cagcagcatc gagaaaacca tcagcaaggc caagggccag    780
cctcgcgagc cccaggtgta cactctgcct ccaagccagg aagagatgac caagaaccag    840
gtgtccctga cctgtctcgt gaagggcttc taccccctccg atatcgccgt ggaatgggag    900
agcaacggcc agcccgagaa caactacaag accacccccc ctgtgctgga cagcgacggc    960
tcattcttcc tgtacagcag actgaccgtg gacaagagcc ggtggcagga aggcaacgtg   1020
ttcagctgca gcgtgatgca cgaggccctg cacaaccact acacccagaa gtccctgagc   1080
ctgagccccg gcaaa                                                    1095
```

<210> SEQ ID NO 9
<211> LENGTH: 245
<212> TYPE: PRT
<213> ORGANISM: Artificial Sequence
<220> FEATURE:
<223> OTHER INFORMATION: Synthetic Peptide

<400> SEQUENCE: 9

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Phe Met Asn Trp Tyr Gln Gln Lys Pro Gly Gln Pro Pro
        35                  40                  45

Lys Leu Leu Ile Tyr Thr Thr Ser Asn Leu Glu Ser Gly Ile Pro Ala
    50                  55                  60

Arg Phe Ser Ala Ser Gly Ser Gly Thr Asp Phe Thr Leu Asn Ile His
65                  70                  75                  80

Pro Val Glu Glu Glu Asp Thr Ala Thr Tyr Tyr Cys Gln Gln Ser Asn
                85                  90                  95

Glu Asp Pro Tyr Thr Phe Gly Gly Gly Thr Lys Leu Glu Leu Lys Arg
            100                 105                 110

Gly Gly Gly Gly Ser Gly Gly Gly Ser Gly Gly Gly Gly Ser Gln
        115                 120                 125

Val Thr Leu Lys Glu Ser Gly Pro Gly Ile Leu Gln Pro Ser Gln Thr
    130                 135                 140

Leu Ser Leu Thr Cys Ser Phe Ser Gly Phe Ser Leu Arg Thr Ser Gly
145                 150                 155                 160

Met Gly Val Gly Trp Ile Arg Gln Pro Ser Gly Lys Gly Leu Glu Trp
                165                 170                 175

Leu Ala His Ile Trp Trp Asp Asp Asp Lys Arg Tyr Asn Pro Ala Leu
```

```
                    180                 185                 190
Lys Ser Arg Leu Thr Ile Ser Lys Asp Thr Ser Asn Gln Val Phe
            195                 200                 205

Leu Lys Ile Ala Ser Val Asp Thr Ala Asp Thr Ala Thr Tyr Tyr Cys
        210                 215                 220

Ala Gln Ile Asn Pro Ala Trp Phe Ala Tyr Trp Gly Gln Gly Thr Leu
225                 230                 235                 240

Val Thr Val Ser Ala
            245

<210> SEQ ID NO 10
<211> LENGTH: 735
<212> TYPE: DNA
<213> ORGANISM: Artificial Sequence
<220> FEATURE:
<223> OTHER INFORMATION: Synthetic Primer

<400> SEQUENCE: 10
gatattgtgc tgacccagag cccggcgagc ctggcggtga gcctgggcca gcgcgcgacc    60
attagctgca aagcgagcca gagcgtggat tttgatggcg atagctttat gaactggtat   120
cagcagaaac cgggccagcc gccgaaactg ctgatttata ccaccagcaa cctggaaagc   180
ggcattccgg cgcgctttag cgcgagcggc agcggcaccg attttaccct gaacattcat   240
ccggtggaag aagaagatac cgcgacctat tattgccagc agagcaacga agatccgtat   300
acctttggcg gcggcaccaa actggaactg aaacgcggcg gcggcggcag cggcggcggc   360
ggcagcggcg gcggcggcag ccaggtgacc ctgaaagaaa gcggcccggg cattctgcag   420
ccgagccaga cgctgagcct gacctgcagc tttagcggct ttagcctgcg caccagcggc   480
atgggcgtgg gctggattcg ccagccgagc ggcaaaggcc tggaatggct ggcgcatatt   540
tggtgggatg atgataaacg ctataacccg gcgctgaaaa gccgcctgac cattagcaaa   600
gataccagca gcaaccaggt gtttctgaaa attgcgagcg tggataccgc ggataccgcg   660
acctattatt gcgcgcagat taacccggcg tggtttgcgt attggggcca gggcaccctg   720
gtgaccgtga gcgcg                                                   735

<210> SEQ ID NO 11
<211> LENGTH: 245
<212> TYPE: PRT
<213> ORGANISM: Artificial Sequence
<220> FEATURE:
<223> OTHER INFORMATION: Synthetic Peptide

<400> SEQUENCE: 11

Glu Val Gln Leu Val Glu Ser Gly Gly Gly Val Val Arg Pro Gly Gly
1               5                  10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Leu Leu Phe Asp Tyr Trp Gly Gln Gly Thr Leu
```

```
            100                 105                 110
Val Thr Val Ser Arg Gly Gly Gly Ser Gly Gly Gly Ser Gly
        115                 120                 125

Gly Gly Gly Ser Gly Gly Gly Ser Ser Glu Leu Thr Gln Asp
        130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
                165                 170                 175

Gly Gln Ala Pro Val Leu Val Ile Tyr Gly Lys Asn Asn Arg Pro Ser
                180                 185                 190

Gly Ile Pro Asp Arg Phe Ser Gly Ser Ser Ser Gly Asn Thr Ala Ser
                195                 200                 205

Leu Thr Ile Thr Gly Ala Gln Ala Glu Asp Glu Ala Asp Tyr Tyr Cys
                210                 215                 220

Asn Ser Arg Asp Ser Ser Gly Asn His Val Val Phe Gly Gly Gly Thr
225                 230                 235                 240

Lys Leu Thr Val Gly
                245

<210> SEQ ID NO 12
<211> LENGTH: 735
<212> TYPE: DNA
<213> ORGANISM: Artificial Sequence
<220> FEATURE:
<223> OTHER INFORMATION: Synthetic Primer

<400> SEQUENCE: 12
gaagtgcagc tggtggaatc tggcggcgga gtcgtgcggc ctggcggatc tctgagactg      60
tcttgtgccg ccagcggctt caccttcgac gactacggca tgagctgggt gcgccaggcc     120
cctggaaaag gcctggaatg ggtgtccggc atcaactgga atggcggcag caccggctac     180
gccgatagcg tgaagggccg gttcaccatc agccgggaca cgccaagaa cagcctgtac      240 ctgcagatga actccctgcg ggccgaggac accgccgtgt actattgtgc cagaggcaga     300
agcctgctgt tcgactactg gggccagggc acactcgtga ccgtgtctag aggcggaggc     360
ggatctgggg gggaggatc tggcggaggg ggaagtgggg gaggcggaag ttctagcgag     420
ctgacacagg accctgccgt gtctgtggcc ctgggacaga cagtgcggat cacctgtcag     480
ggcgacagcc tgagaagcta ctacgccagc tggtatcagc agaagcccgg acaggctccc     540
gtgctcgtga tctacggcaa gaacaaccgg cccagcggca tccccgatag attcagcggc     600
agcagcagcg gcaataccgc cagcctgaca atcactggcg cccaggccga ggatgaggcc     660
gactactact gcaacagcag agacagctcc ggcaatcacg tggtgttcgg cggaggcacc     720
aagctgacag tggga                                                       735

<210> SEQ ID NO 13
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 13

Met Asp Trp Ile Trp Arg Ile Leu Phe Leu Val Gly Ala Ala Thr Gly
1               5                   10                  15

Ala His Ser
```

```
<210> SEQ ID NO 14
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 14

Met Ala Leu Pro Val Thr Ala Leu Leu Leu Pro Leu Ala Leu Leu Leu
1               5                   10                  15

His Ala Ala Arg Pro
            20

<210> SEQ ID NO 15
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 15

Met Glu Phe Gly Leu Ser Trp Leu Phe Leu Val Ala Ile Leu Lys Gly
1               5                   10                  15

Val Gln Cys Ser Arg
            20
```

CANCER GENE THERAPY TARGETING CD47

This application is a national phase application under 35 U.S.C. § 371 that claims priority to International Application No. PCT/US2017/028050 filed Apr. 18, 2017, which claims priority to U.S. Provisional Patent Application Ser. No. 62/323,926, filed Apr. 18, 2016, all of which are incorporated herein by reference in their entirety.

STATEMENT REGARDING FEDERALLY SPONSORED RESEARCH OR DEVELOPMENT

This invention was made with government support under 1F30CA203270-01 awarded by National Institutes of Health. The government has certain rights in the invention.

TECHNICAL FIELD

Embodiments of the disclosure encompass at least the fields of cell biology, molecular biology, immunology, and medicine, including at least cancer medicine.

BACKGROUND

There is a need to improve outcomes for patients with metastatic solid tumors. Solid tumors account for the majority of cancer-related cases and deaths in the world.[1] Outcomes remain especially poor for patients with unresectable, refractory, or recurrent solid tumors.[2] Thus, there is a need for novel targeted therapies for these patients.

Tumor associated macrophages (TAMs) are present within the tumor microenvironment. While macrophages normally phagocytose and kill tumor cells, TAMs promote tumor growth.[3] Other investigators have shown that tumor cells express high levels of CD47 that binds to signal-regulatory protein alpha (SIRPα), an inhibitory receptor on macrophages, allowing tumor cells to evade phagocytosis.[4] Thus, CD47 has been termed a "don't eat me signal." Recent studies have shown that blocking CD47 with a monoclonal antibody with an IgG4 constant region (IgG4-Fc (fragment crystallizable region)) or a fusion protein consisting of the soluble ectodomain of SIRPα or a derivative thereof (e.g. CV1) and IgG4-Fc (SIRPα-Fc) has potent antitumor activity in preclinical animal models.[5] The Fc portion of IgG4 was chosen because it does not fix complement but binds hFcγRI expressed on macrophages with high affinity.[6] Interestingly, the soluble ectodomain of SIRPa by itself had little antitumor activity, highlighting that CD47 blocking and opsonization are useful for the observed therapeutic effect.[5] However, there are significant safety concerns in regards to the systemic administration of SIRPα-Fc.[7] The present disclosure provides a need in the art for blocking CD47 at least to redirect tumor associated macrophages (TAMs) to tumor cells.

BRIEF SUMMARY

Embodiments of the disclosure concern methods and compositions for treating cancer in an individual. The individual may be a mammal of any kind, and the cancer may be of any kind that has a solid mass, including at least breast, lymphoma, brain, lung, pancreatic, liver, colon, skin, blood, bone, kidney, ovarian, testicular, cervical, endometrial, head and neck, stomach, gall bladder, prostate, thyroid, spleen, bladder, rectal, pituitary gland, and so forth. In particular embodiments, at least some of the cancer cells in the individual express Cluster of Differentiation 47 (CD47).

In certain embodiments, the disclosure concerns gene therapy that facilitates the efficacious targeting of tumor associated macrophages (TAMs) to tumor cells. Specific embodiments provide the redirection of TAMs to tumor cells. Such embodiments employ the blockage of a certain cell surface molecule on the surface of cancer cells, including at least CD47 (which may also be known as integrin associated protein (IAP); MERG; or OA3). Thus, gene therapy of the present disclosure facilitates efficacious targeting of TAMs to tumor cells that express CD47, in certain embodiments.

Some embodiments of the disclosure concern gene therapy using delivery of a polynucleotide encoding a secretable form of a protein that can bind CD47 and bind a FC receptor (the SIRPα-Fc fusion protein, for example) into tumor cells and/or cells within the tumor microenvironment. Once the gene is delivered into cells, cells start to produce and secrete SIRPα-Fc (as an example) within the solid tumor mass. This is superior to the direct infusion (including intermittent) of the protein at least because of the following: 1) the concentration of SIRPα-Fc is highest at tumor sites, and 2) local production reduces the risks of unwanted systemic side effects.

In one embodiment, there is a composition comprising a polynucleotide encoding: a) a CD47-binding entity; and b) an FC receptor-binding entity, wherein both entities are encoded from the polynucleotide as a fusion protein and the fusion protein is secretable. In specific embodiments, the polynucleotide encodes a leader sequence operably linked to the fusion protein. In particular embodiments, the polynucleotide encodes a label or tag that is operatively linked to the fusion protein. In certain cases, the CD47-binding entity comprises an antibody or functional antibody fragment thereof, such as an antibody being an scFv or a monoclonal antibody. In some cases, the CD47-binding entity comprises a signal-regulatory protein alpha (SIRPα) ectodomain or a functional derivative thereof. The FC receptor-binding entity may comprise an IgG constant region, such as the IgG constant region being from IgG4, IgG1, or IgG2. In certain cases, the FC receptor-binding entity comprises a monoclonal antibody that binds an FC receptor, such as when a FC receptor-binding entity comprises a scFv that binds an FC receptor.

In certain polynucleotide compositions, in a 5' to 3' orientation on the polynucleotide the CD47-binding entity is in a 5' position upstream of the FC receptor-binding entity on the polynucleotide, although in some cases in a 5' to 3' orientation on the polynucleotide, the CD47-binding entity is in a 3' position downstream of the FC receptor-binding entity on the polynucleotide. Any polynucleotides may be comprised on a vector, such as a viral vector or a non-viral vector. In certain examples, the viral vector is a lentiviral vector, vaccinia virus, adenoviral vector, adeno-associated viral vector, Herpes simplex viral vector, myxoma viral vector, reoviral vector, polio viral vector, vesicular stomatitis viral vector, measles viral vector, Newcastle disease viral vector, or retroviral vector. In particular cases, a non-viral vector is a plasmid, nanoparticle, cationic lipid, cationic polymer, lipid polymer, liposome, or combination thereof. Polynucleotides of the disclosure may be DNA or RNA.

In certain embodiments, compositions of the disclosure comprise an additional cancer therapy, such as a polynucleotide, peptide, protein, small molecule, or combination thereof. In cases wherein the additional cancer therapy comprises a polynucleotide, the additional cancer therapy polynucleotide and the polynucleotide that encodes the fusion protein are the same polynucleotide molecule, although in some cases they are different polynucleotide molecules. An additional cancer therapy polynucleotide may encode a gene product that comprises immune stimulatory function, such as a gene product that comprises immune stimulatory function comprises one or more cytokines, one or more chemokines, one or more costimulatory molecules, one or more antibody-comprising molecules, one or more gene products that edit the genome or silence gene expression of cancer cells and/or other cells within the tumor microenvironment, or a combination thereof. Cytokines may be selected from the group consisting of IL2, IL7, IL12, IL15, IL21, and a combination thereof. Chemokines may be from the CXC, CC, CX3C, or XC family. Costimulatory molecules may be selected from the group consisting of CD70, CD80, CD86, CD134L, CD137L, other tumor necrosis superfamily members, and a combination thereof.

When the additional therapy comprises one or more antibody-comprising molecules, the antibody may be a bispecific antibody. The one or more antibody-comprising molecules may comprise a chimeric antigen receptor, a bi-specific T-cell engager (BITE), or a Dual-Affinity Re-Targeting (DART) molecule. The one or more gene products that edit the genome or silence gene expression of cancer cells and/or other cells within the tumor microenvironment may comprise shRNAs, zinc finger nucleases, TALENs, and/or CRIPR/Cas9 genes that silence or knock out negative regulators, for example. The CRIPR/Cas9 genes that silence or knock out negative regulators may comprise CTLA4, PD1, PD-L1, TIM3, LAG3, IDO, or a combination thereof.

In one embodiment, there is a method of treating cancer in an individual, comprising the step of locally or systemically delivering to one or more tumors and/or tumor microenvironments of the individual an effective amount of a composition of the disclosure. The composition may be delivered in vivo or ex vivo. The ex vivo delivery may comprise the step of modifying one or more cells to harbor the composition prior to delivering the one or more cells to the one or more tumors and/or tumor microenvironments of the individual. The one or more cells may be autologous, allogeneic, or xenogeneic to the individual. In specific embodiments, tumor cells and/or cells in the tumor microenvironment are modified by the composition to express a fusion protein of the polynucleotide. Cells in the tumor microenvironment may comprise stroma cells, endothelial cells, immune cells, or a combination thereof. In some cases, the method further comprises the step of delivering an additional cancer therapy to the individual, such as wherein the additional cancer therapy is comprised in the composition, although the additional cancer therapy may not be comprised in the composition. In some cases, the cancer has at least one solid mass.

In one embodiment, there is a method of sensitizing cancer cells to immune cells in an individual, comprising the step of delivering to the individual an effective amount of a composition encompassed by the disclosure.

BRIEF DESCRIPTION OF THE DRAWINGS

(FIG. 1A) FACS analysis of OV10, a CD47-negative human ovarian cancer cell line (white) and OV10 315, genetically modified to express CD47 (black) Anti-human CD47-APC (clone: B6H12) (eBioscience). (FIG. 1B) Human cells that express CD47 include Raji (Burkitt's lymphoma), U373 (glioblastoma), and peripheral blood mononuclear cells (PBMCs) from a healthy donor. Anti-human CD47 antibody (black) and isotype (white). Isotype was mouse anti-human IgG1. (FIG. 1C) Murine cells that express CD47 include B16 (melanoma), MC38 (adenocarcinoma), and splenocytes from a C57/B6 mouse. Anti-murine CD47 antibody (black) and isotype (white). Anti-murine CD47-APC (clone: miap301) (eBioscience). Isotype: Rat anti-mouse IgG2a.

(FIG. 2A) Schematic of lentiviral vectors expressing either SIRPα or SIRPα-Fc. HA: HA epitope tag. GFPpuro: Green fluorescent protein and puromycin resistance gene for detection and selection. In the generated lentiviral vectors we used the derivative of the SIRPα ectodomain CV1. (FIG. 2B) Transduction efficacy of 4 cell lines transduced with pCDH.CMV.SIRPα.EF1.GFPpuro or with pCDH.CMV.SIRPα-Fc.EF1.GFPpuro, as measured by GFP expression. Transduction was greater than 90% after selection with puromycin for OV10 315, B16, MC38, and Raji. (FIG. 2C) Fc is only detected on cells transduced to express SIRPα-Fc and not on non-transduced (NT) or SIRPα-expressing cells. OV10 315 and MC38 chosen as representative cells lines for human and mouse, respectively. (FIG. 2D) Both SIRPα and SIRPα-Fc expression block detection of CD47 using an anti-CD47 antibody, though there is a greater shift with SIRPα-Fc.

FIGS. 5A-5C: Demonstration that SIRPα-Fc-expressing tumor cells have reduced tumorigenicity in both xenograft and immune-competent mouse models. (FIG. 5A) NSG mice were injected i.v. with 2×10^5 Raij, Raij-SIRPα, or Raij-SIRPα-FC cells (n=5 per group). While Raij or Raij-SIRPα injected mice started to lose weight (wt) and needed to be euthanized, 3/5 Raij-SIRPα-FC injected mice consistently gained weight and did not develop tumors (Raij vs Raij-SIRPα-FC: p<0.05; Raij vs Raij-SIRFα: p=NS; Raij- SIRPα vs Raij-SIRPα-FC: p<0.05 with logrank test). (FIG. 5B) C57BL/6 mice were injected s.c. with 1×10^6 B16, B16-SIRPα, or B16-SIRPα-FC cells (n=5 per group). Tumor size was monitored by caliper measurements. While there was no difference in tumor growth, the tumorigenicity of B16-SIRPα-FC was greatly reduced leading to a survival advantage (B16 vs B16-SIRPα-FC: p<0.05; B16 vs B16-SIRFα: p=NS; B16-SIRPα vs B16-SIRPα-FC: p<0.05 with logrank test). (FIG. 5C) C57BL/6 mice were injected s.c. with 1×10^6 MC38, MC38-SIRPα, or MC38-SIRPα-FC cells (n=4-5 per group). Tumor size was monitored by caliper measurements. 4/4 MC38 mice developed tumors and eventually had to be euthanized while only 1/5 MC38-SIRPα and 1/5 MC38-SIRPα-FC mice developed tumors.

FIGS. 6A-6B: Demonstration that oncolytic vaccinica virus (VV) can be genetically modified to express SIRPα or SIRPα-Fc. (FIG. 6A) Schematic of VV shuttle plasmid: The expression cassette consists of a late F17R promoter for SIRPα or SIRPα-FC expression and the early/late Pse/I promoter for expression of the marker gene yellow fluorescent protein (YFP). The expression cassette is flanked by viral sequences corresponding to left (L) and right (R) viral TK (vTK) locus. In the generated VVs the derivative of the SIRPα ectodomain CV1 was used. (FIG. 6B) PCR confirms presence of transgene. VVs were generated by homologous recombination, and the integrity of the inserted transgene was confirmed by sequencing. Shuttle plasmids bearing SIRPα (pCMS1-SIRPα) and SIRPα-Fc (pCMS1-SIRPα-Fc) were positive controls. DNA was isolated from VVs expressing SIRPα or SIRPα-Fc and PCR was performed using primers targeted to a region of the shuttle plasmid either upstream or downstream of the transgene.

(FIG. 7A) The oncolytic killing of the SIRPα-VV and SIRPα-Fc-VV are similar. OV10 315 cells were infected with indicated virus at MOI 0.1 and cells were harvested for FACS analysis at 24, 48, and 72 hours post-infection. Cells were stained with 7AAD, a marker for cell death, and either anti-Fc or anti-CD47 antibody. Cell death as measured by 7AAD incorporation increased over time for both SIRPα-VV and SIRPα-Fc-VV. YFP was used to detect cells infected with virus, and it also increased over time. (FIG. 7B) Fc can only be detected on cells infected with SIRPα-Fc-VV and not uninfected cells or SIRPα-VV-infected cells 24 post-infection. (FIG. 7C) CD47 cannot be detected on cells infected with SIRPα-VV or SIRPα-Fc-VV but can be detected on non-infected cells 48 hours post-infection.

DETAILED DESCRIPTION

Figure 1A:
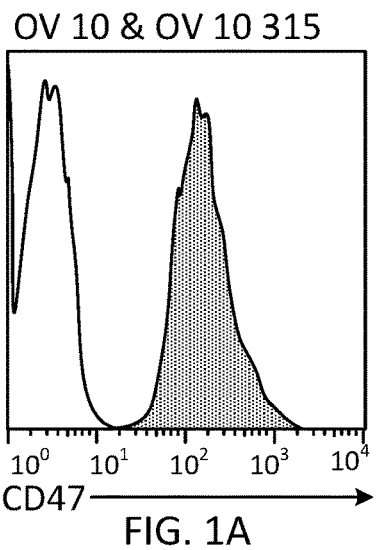
FIGS. 1A-1C: Demonstration that CD47 is expressed on a range of human and murine cell lines.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. The scope of the present application is not intended to be limited to the particular embodiments of the process, machine, manufacture, composition of matter, means, methods and steps described in the specification.

I. General Embodiments

Embodiments of the disclosure allow for enhanced use of native immune cells, such as TAMs, to target CD47-bearing cancer cells. The TAMs are able to avoid blockage of their own activity from CD47-bearing cancer cells upon use of one or more composition(s) to block CD47 activity at a localized tumor or tumor microenvironment in an individual in need thereof. In particular, embodiments of the disclosure provide that TAMs have enhanced activity or maintained activity or reestablished activity upon targeting and blocking of CD47 on cancer cells. The compositions for blocking CD47 are also able to activate immune cells that express FC receptors, including the TAMs, and upon activation the immune system is then stimulated to eradicate cancer cells.

Embodiments of the disclosure provide a gene therapy approach that sensitizes tumor cells to macrophages and other immune cells that express FC receptors, including but not limited to natural killer cells, neutrophils, eosinophils, and basophils, resulting in potent antitumor activity. In addition, the gene therapy approach also sensitizes tumor cells to immune cells that only express the natural ligand of CD47 such as dendritic cells. Specific embodiments concern targeting of CD47-expressing tumor cells to inhibit activity of CD47 such that tumor macrophages and/or other immune cells are then able to more easily phagocytose and kill the tumor cells.

In certain embodiments, to overcome present limitations to block CD47, provided herein is a cancer gene therapy approach in which tumor cells and/or cells within the tumor microenvironment are genetically modified to secrete a molecule that at least effectively blocks CD47. Such a molecule may be a fusion molecule having one entity that blocks CD47 and a second entity that binds a FC receptor on an immune cell for subsequent activation of the immune cell. In particular cases, the fusion protein comprises a SIRPα ectodomain or a derivate thereof operably linked to an entity that binds FC receptors. Specific embodiments show that tumor cells, which are genetically modified with lentiviral vectors (merely an example of a vector) to secrete SIRPα-Fc, are i) recognized and killed by macrophages, and ii) grow slower or are rejected in mice. In addition, it is demonstrated herein that oncolytic vaccinia viruses (as an example of a vector) are also suitable gene delivery vehicle to express SIRPα-Fc in tumor cells.

II. Examples of Compositions

Compositions of the disclosure comprise polynucleotides that encode a fusion protein that comprises at least a CD47-binding entity and an FC receptor-binding entity such that the fusion protein has activity to bind CD47 and to bind an FC receptor, either separately or simultaneously; it may be referred to herein as a CD47-binding fusion protein.

In any molecule encompassed by the disclosure, there is at least a CD47-binding entity that may be of any kind. In some cases the CD47-binding entity is a ligand or some form of antibody or some form of a receptor that is able to directly bind at least part of CD47. In specific cases, the ectodomain of a CD47-binding receptor is utilized in the composition as the CD47-binding entity. One example of a CD47-binding receptor is the receptor SIRPα and its ectodomain (or derivative, e.g. CV1, Weiskopf et al. Science 2013) that physically interacts with CD47 may be employed in the composition as the CD47-binding entity. As an example below sequences of two SIRPα-IgG4 Fc fusion proteins are shown:

```
SIRPα-IgG4 Fc with native SIRPα ectodomain-amino acid sequence:
Leader sequence
                                                         (SEQ ID NO: 1)
MDWIWRILFLVGAATGAHS SIRPα ectodomain (native)
                                                         (SEQ ID NO: 2)
EEELQVIQPDKSVLVAAGETATLRCTATSLIPVGPIQWFRGAGPGRELIYNQKEG
HFPRVTTVSDLTKRNNMDFSIRIGNITPADAGTYYCVKFRKGSPDDVEFKSGTELSVRAK
PS IgG4 FC
                                                         (SEQ ID NO: 3)
AAAPPCPPCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWESNGQPENNYK
TTPPVLDSDGSFFLYSRLTVDKSRWQEGNVFSCSVMHEALHNHYTQKSLSLSPGK SIRPα-IgG4 Fc with native SIRPα ectodomain-nucleotide sequence:
                                                         (SEQ ID NO: 4)
ATGGACTGGATCTGGCGGATCCTGTTCCTCGTGGGAGCCGCCACAGGCGCCC
ACTCTGAAGAGGAACTGCAAGTGATCCAGCCCGACAAGAGCGTGCTGGTGGCCGCT
GGCGAAACCGCCACCCTGAGATGTACAGCCACCAGCCTGATCCCCGTGGGCCCCAT
CCAGTGGTTTAGAGGCGCTGGCCCTGGCAGAGAGCTGATCTACAACCAGAAAGAGG
GCCACTTCCCCAGAGTGACCACCGTGTCCGACCTGACCAAGCGGAACAACATGGAC
TTCAGCATCCGGATCGGCAACATCACCCCTGCCGATGCCGGCACCTACTACTGCGTG
AAGTTCCGGAAGGGCAGCCCCGACGACGTGGAATTCAAGAGCGGCACCGAGCTGAG
CGTGCGGGCCAAACCTTCTGCTGCCGCTCCTCCTTGCCCTCCATGTCCTGCCCCTGAG
TTTCTGGGCGGACCCAGCGTGTTCCTGTTCCCCCCAAAGCCCAAGGACACCCTGATG
ATCAGCCGGACCCCCGAAGTGACCTGCGTGGTGGTGGATGTGTCCCAGGAAGATCC
CGAGGTGCAGTTCAATTGGTACGTGGACGGCGTGGAAGTGCACAACGCCAAGACCA
AGCCCAGAGAGGAACAGTTCAACAGCACCTACCGGGTGGTGTCCGTGCTGACCGTG
CTGCACCAGGACTGGCTGAACGGCAAAGAGTACAAGTGCAAGGTGTCCAACAAGGG
CCTGCCCAGCAGCATCGAGAAAACCATCAGCAAGGCCAAGGGCCAGCCTCGCGAGC
CCCAGGTGTACACACTGCCTCCAAGCCAGGAAGAGATGACCAAGAACCAGGTGTCC
CTGACCTGTCTCGTGAAGGGCTTCTACCCCTCCGATATCGCCGTGGAATGGGAGAGC
AACGGCCAGCCCGAGAACAACTACAAGACCACCCCCCCTGTGCTGGACAGCGACGG
CTCATTCTTCCTGTACAGCAGACTGACCGTGGACAAGAGCCGGTGGCAGGAAGGCA
ACGTGTTCAGCTGCAGCGTGATGCACGAGGCCCTGCACAACCACTACACCCAGAAG
TCCCTGAGCCTGAGCCCCGGCAAA
```

SIRPα-IgG4 Fc with derivative (CV1) of SIRPα ectodomain-amino acid sequence
Leader sequence
(SEQ ID NO: 5)
MDWIWRILFLVGAATGAHS SIRPα ectodomain (CV1 derivative)
(SEQ ID NO: 6)
EEELQIIQPDKSVLVAAGETATLRCTITSLFPVGPIQWFRGAGPGRVLIYNQRQGP
FPRVTTVSDTTKRNNMDFSIRIGNITPADAGTYYCIKFRKGSPDDVEFKSGAGTELSVRA
KPS IgG4 FC
(SEQ ID NO: 7)
AAAPPCPPCPAPEFLGGPSVFLFPPKPKDTLMISRTPEVTCVVVDVSQEDPEVQFN
WYVDGVEVHNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEWESNGQPENNYK
TTPPVLDSDGSFFLYSRLTVDKSRWQEGNVFSCSVMHEALHNHYTQKSLSLSPGK SIRPα-IgG4 Fc with derivative (CV1) of SIRPα ectodomain-nucleotide sequence
(SEQ ID NO: 8)
ATGGACTGGATCTGGCGGATCCTGTTCCTCGTGGGAGCCGCCACAGGCGCCC
ACTCTGAAGAGGAACTGCAGATCATCCAGCCCGACAAGAGCGTGCTGGTGGCCGCT
GGCGAAACCGCCACCCTGAGATGTACCATCACCAGCCTGTTCCCTGTGGGCCCCATC
CAGTGGTTTAGAGGCGCCGGACCTGGCCGGGTGCTGATCTACAATCAGAGACAGGG
CCCCATTCCCCAGAGTGACCACCGTGTCCGACACCACCAAGCGGAACAACATGGACT
TCAGCATCCGGATCGGCAACATCACCCCTGCCGATGCCGGCACCTACTACTGCATCA
AGTTCCGGAAGGGCAGCCCCGACGACGTGGAATTCAAAAGCGGAGCCGGCACCGA
GCTGAGCGTGCGGGCTAAACCTTCTGCCGCCGCTCCTCCTTGCCCTCCATGTCCTGCC
CCTGAGTTTCTGGGCGGACCCAGCGTGTTCCTGTTCCCCCCAAAGCCCAAGGACACC
CTGATGATCAGCCGGACCCCCGAAGTGACCTGCGTGGTGGTGGATGTGTCCCAGGA
AGATCCCGAGGTGCAGTTCAATTGGTACGTGGACGGCGTGGAAGTGCACAACGCCA
AGACCAAGCCCAGAGAGGAACAGTTCAACAGCACCTACCGGGTGGTGTCCGTGCTG
ACCGTGCTGCACCAGGACTGGCTGAACGGCAAAGAGTACAAGTGCAAGGTGTCCAA
CAAGGGCCTGCCCAGCAGCATCGAGAAAACCATCAGCAAGGCCAAGGGCCAGCCTC
GCGAGCCCCAGGTGTACACACTGCCTCCAAGCCAGGAAGAGATGACCAAGAACCAG
GTGTCCCTGACCTGTCTCGTGAAGGGCTTCTACCCCTCCGATATCGCCGTGGAATGG
GAGAGCAACGGCCAGCCCGAGAACAACTACAAGACCACCCCCCCTGTGCTGGACAG
CGACGGCTCATTCTTCCTGTACAGCAGACTGACCGTGGACAAGAGCCGGTGGCAGG
AAGGCAACGTGTTCAGCTGCAGCGTGATGCACGAGGCCCTGCACAACCACTACACC
CAGAAGTCCCTGAGCCTGAGCCCCGGCAAA In some cases, an antibody that binds CD47 is utilized in the composition as the CD47-binding entity. The antibody may be of any kind including CD47-specific monoclonal antibodies in any format (for example, but not limited to, single chain variable format (scFv)). The antibody may be commercially obtained or produced using routine methods in the art.

The compositions of the disclosure comprise a FC receptor-binding entity, in particular embodiments. In particular cases, the FC receptor-binding entity is any kind of molecule that can bind at least one type of FC receptor on an immune cell, thereby stimulating function of the immune cell. In specific embodiments, the FC receptor-binding activity can bind a FC receptor on a TAM. In particular cases, the FC receptor-binding entity comprises the Fc portion of an antibody, including for example, the constant region of IgG1, IgG2, or IgG4. In specific cases, the FC receptor-binding entity may be a monoclonal antibody, including a scFv, that is specific for FC receptors, for example, but not limited to, scFvs that recognize the Fc receptor CD16 (scFv 3G8 or NM3E2):

3G8 amino acid sequence
(SEQ ID NO: 9)
DIVLTQSPASLAVSLGQRATISCKASQSVDFDGDSFMNWYQQKPGQPPKL
LIYYTSSNLESGIPARFSASGSGTDFTLNIHPVEEEDTATYYCQQSNEDPY
TFGGGTKLELKRGGGGSGGGGSGGGGSQVTLKESGPGILQPSQTLSLTCS
FSGFSLRTSGMGVGWIRQPSGKGLEWLAHIWWDDDKRYNPALKSRLTISK
DTSSNQVFLKIASVDTADTATYYCAQINPAWFAYWGQGTLVTVSA 3G8 nucleotide sequence
(SEQ ID NO: 10)
GATATTGTGCTGACCCAGAGCCCGGCGAGCCTGGCGGTGAGCCTGGGCCA
GCGCGCGACCATTAGCTGCAAAGCGAGCCAGAGCGTGGATTTTGATGGCG
ATAGCTTTATGAACTGGTATCAGCAGAAACCGGGCCAGCCGCCGAAACTG
CTGATTTATACCACCAGCAACCTGGAAAGCGGCATTCCGGCGCGCTTTAG
CGCGAGCGGCAGCGGCACCGATTTTACCCTGAACATTCATCCGGTGGAAG
AAGAAGATACCGCGACCTATTATTGCCAGCAGAGCAACGAAGATCCGTAT
ACCTTTGGCGGCGGCACCAAACTGGAACTGAAACGCGGCGGCGGCGGCAG
CGGCGGCGGCGGCAGCGGCGGCGGCGGCAGCCAGGTGACCCTGAAAGAAA
GCGGCCCGGGCATTCTGCAGCCGAGCCAGACCCTGAGCCTGACCTGCAGC
TTTAGCGGCTTTAGCCTGCGCACCAGCGGCATGGGCGTGGGCTGGATTCG
CCAGCCGAGCGGCAAAGGCCTGGAATGGCTGGCGCATATTTGGTGGGATG
ATGATAAACGCTATAACCCGGCGCTGAAAAGCCGCCTGACCATTAGCAAA
GATACCAGCAGCAACCAGGTGTTTCTGAAAATTGCGAGCGTGGATACCGC -continued

GGATACCGCGACCTATTATTGCGCGCAGATTAACCCGGCGTGGTTTGCGT

ATTGGGGCCAGGGCACCCTGGTGACCGTGAGCGCG

NM3E2 amino acid sequence
(SEQ ID NO: 11)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSRGGGGSGGGGSGGGGSGGGGSSSELTQDPAVSVA

LGQTVRITCQGDSLRSYYASWYQQKPGQAPVLVIYGKNNRPSGIPDRFSG

SSSGNTASLTITGAQAEDEADYYCNSRDSSGNHVVFGGGTKLTVG

NM3E2 nucleotide sequence
(SEQ ID NO: 12)
GAAGTGCAGCTGGTGGAATCTGGCGGCGGAGTCGTGCGGCCTGGCGGATC

TCTGAGACTGTCTTGTGCCGCCAGCGGCTTCACCTTCGACGACTACGGCA

TGAGCTGGGTGCGCCAGGCCCCTGGAAAAGGCCTGGAATGGGTGTCCGGC

ATCAACTGGAATGGCGGCAGCACCGGCTACGCCGATAGCGTGAAGGGCCG

GTTCACCATCAGCCGGGACAACGCCAAGAACAGCCTGTACCTGCAGATGA

ACTCCCTGCGGGCCGAGGACACCGCCGTGTACTATTGTGCCAGAGGCAGA

AGCCTGCTGTTCGACTACTGGGGCCAGGGCACACTCGTGACCGTGTCTAG

AGGCGGAGGCGGATCTGGGGGGGAGGATCTGGCGGAGGGGGAAGTGGGG

GAGGCGGAAGTTCTAGCGAGCTGACACAGGACCCTGCCGTGTCTGTGGCC

CTGGGACAGACAGTGCGGATCACCTGTCAGGGCGACAGCCTGAGAAGCTA

CTACGCCAGCTGGTATCAGCAGAAGCCCGGACAGGCTCCCGTGCTCGTGA

TCTACGGCAAGAACAACCGGCCCAGCGGCATCCCCGATAGATTCAGCGGC

AGCAGCAGCGGCAATACCGCCAGCCTGACAATCACTGGCGCCCAGGCCGA

GGATGAGGCCGACTACTACTGCAACAGCAGAGACAGCTCCGGCAATCACG

TGGTGTTCGGCGGAGGCACCAAGCTGACAGTGGGA

In specific examples, the polynucleotide encodes a sequence that allows the fusion protein to be secretable from a cell, such as a leader or signal sequence. The leader sequence is configured on the fusion protein appropriately so that any cell in which the polynucleotide resides may express the fusion protein and allow the fusion protein to become secreted so that it may act upon other cells. In specific embodiments, the leader sequence is about 5-30 amino acids long and is present at the N-terminus of the fusion protein. In at least some cases, a core of the leader sequence (which may also be referred to as a signal peptide) contains a long stretch of hydrophobic amino acids that has a tendency to form a single alpha-helix. Examples in amino acid format include but are not limited to the following: MDWIWRILFLVGAATGAHS (SEQ ID NO: 13), MALPVTALLLPLALLLHAARP (SEQ ID NO: 14), or MEFGLSWLFLVAILKGVQCSR (SEQ ID NO: 15). A complete list of mammalian leader or signaling sequences (13, 094) can be found at http://www.signalpeptide.de/index.php?m=listspdb_mammalia.

The polynucleotide of the disclosure may be DNA or RNA.

In some embodiments, the polynucleotide is comprised in or on a vector. The vector may or may not be oncolytic. While in specific embodiments lentiviral vectors or vaccinia viruses to deliver a polynucleotide encoding SIRPα-Fc into tumor cells may be used, any viral or non-viral vector may be used in vivo or ex vivo to deliver the polynucleotides into tumor cells and/or cells within the tumor microenvironment. This includes, but is not limited to, adenovirus (replication competent, replication incompetent, helper dependent), adeno associated virus (AAV), Herpes simplex virus 1 (HSV1), myxoma virus, reovirus, poliovirus, vesicular stomatitis virus (VSV), measles virus (MV), Newcastle disease virus (NDV), retroviruses, nanoparticles, cationic lipids, cationic polymers, and/or lipid polymers, for example. The polynucleotide may be generated as part of the same molecule as a vector, the polynucleotide may be encompassed within a vector, and/or the polynucleotide may be attached to a vector, as examples.

The polynucleotide of the disclosure is a non-natural polynucleotide that may be generated by any means, including by standard recombinant methods known in the art, for example. The CD47-binding entity and the FC receptor-binding entity reside on the polynucleotide in a functionally operable configuration, such that upon translation of the polynucleotide the CD47-binding entity and the FC receptor-binding entity are produced as a single polypeptide. Once produced as a fusion protein, the CD47-binding entity may be N-terminal or C-terminal in relation to the FC receptor-binding entity.

Utilized in the examples herein is an example of a fusion polynucleotide that comprises a leader sequence, the ectodomain of SIRPa or a derivative thereof, and the Fc portion of IgG4.

III. Examples of Methods of Use of the Compositions

Any method of using one or more compositions of the disclosure is encompassed herein. The method of using the composition(s) may be to treat cancer, to sensitize tumor cells to macrophages in an individual, to enhance the activity of endogenous TAMs, other FC receptor expressing cells, or antigen presenting cells, to block CD47 activity on a cancer cell, and so forth.

Polynucleotides of the disclosure encode fusion proteins that block CD47 activity, and the fusion protein(s) may be generated for and/or in an individual in any manner. In some cases, the polynucleotide is delivered to the individual locally such that upon delivery of the polynucleotide composition to a tumor and/or tumor microenvironment in vivo, the polynucleotide is taken up by tumor cells and/or cells of the tumor microenvironment, and the fusion protein is produced in those cells. Following production of the fusion protein in the cells, the cells secrete the fusion protein such that it is soluble and can bind its target(s) on other cells, including at least non-transduced cells, and in particular cancer cells.

In some embodiments, a polynucleotide encoding the fusion protein is transfected into cells ex vivo and the cells harboring the polynucleotide are locally delivered to tumors and/or tumor microenvironment such that the ex vivo-manipulated cells produce the fusion protein and then secrete the fusion protein such that it is soluble and can bind its target(s) on other cells, including at least non-transduced cells, and in particular cancer cells. The cells that are manipulated ex vivo may be autologous, allogeneic, syngeneic, or xenogeneic in relation to the individual. In cases wherein the cells to be manipulated ex vivo come from the individual to be treated, the cells may be obtained following diagnosis of the cancer in the individual or the cells may be obtained from a cell repository that harbors the cells for the individual. Any cells to be manipulated ex vivo may or may not be immune cells.

When the polynucleotide compositions of the disclosure are provided locally to the individual, they may be taken up by tumor cells within a solid mass or they may be taken up by any cell within the tumor microenvironment, for example but not limited to stroma cells, endothelial cells, and immune cells within the tumor microenvironment.

The polynucleotide composition, whether or not it is comprised in or on a vector, may be delivered locally to an individual in any suitable manner. In some cases the polynucleotide is delivered to the individual when it is not contained within a cell, although in other cases the polynucleotide is contained within a cell. In any event, any physical method for delivery may be used to deliver the polynucleotide (for example, but not limited to gene gun, electroporation, hydrodynamic, ultrasound, direct injection, intravenous intra-arterial injection, and so forth).

In some methods of the disclosure, the gene therapy approach is combined with the delivery of other polynucleotides (including polynucleotides that encode at least one therapeutic molecule) and/or other types of cancer therapies. In some cases, one or more additional cancer therapies are provided as part of the same composition as the composition that comprises the polynucleotide that encodes the CD47-binding fusion protein. For example, other polynucleotides that encode gene products that have immune stimulatory function, for example, may be provided in the same or different compositions as the CD47-binding fusion protein. For example, but not limited to, polynucleotides that encode cytokines (IL2, IL7, IL12, IL15, IL21), chemokines belonging to one of four families (CXC, CC, CX3C and XC), costimulatory molecules (CD70, CD80, CD86, CD134L, CD137L, and other tumor necrosis factor (TNF) superfamily members), and antibodies or bispecific antibodies of any format (BITE, DART) may be utilized, although in some cases the protein that is encoded by the polynucleotide is delivered instead. In addition, polynucleotides that edit the genome or silence gene expression of cancer cells and/or other cells within the tumor microenvironment could be co-delivered with the polynucleotides of the disclosure, including the exemplary SIRPα-Fc fusion gene.

By way of illustration, cancer patients or patients susceptible to cancer or suspected of having cancer may be treated as described herein. The polynucleotides and/or cells modified as described herein may be administered to the individual and retained for extended periods of time. The individual may receive one or more administrations of the polynucleotides and/or cells and/or additional cancer therapies. In some embodiments, polynucleotides and/or genetically modified cells are encapsulated to inhibit immune recognition and placed at the site of the tumor.

In various embodiments the expression constructs, nucleic acid sequences, vectors, host cells and/or pharmaceutical compositions comprising the same are used for the prevention, treatment or amelioration of a cancerous disease, such as a tumorous disease. In particular embodiments, the pharmaceutical composition of the present disclosure may be particularly useful in preventing, ameliorating and/or treating cancer, including cancer having solid tumors, for example.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve either the reduction or amelioration of symptoms of the disease or condition and/or the delaying of the progression of the disease or condition. "Treatment" does not necessarily indicate complete eradication or cure of the disease or condition, or associated symptoms thereof.

In particular embodiments, the present disclosure contemplates, in part, cells harboring expression constructs, nucleic acid molecules and/or vectors that can be administered either alone or in any combination with another therapy, and in at least some aspects, together with a pharmaceutically acceptable carrier or excipient. In certain embodiments, in ex vivo cases prior to administration of the cells, said nucleic acid molecules or vectors may be stably integrated into the genome of the cells. In specific embodiments, viral vectors may be used that are specific for certain cells or tissues and persist in said cells. Suitable pharmaceutical carriers and excipients are well known in the art. The compositions prepared according to the disclosure can be used for the prevention or treatment or delaying the above identified diseases.

Furthermore, the disclosure relates to a method for the treatment or amelioration of a cancerous (including tumorous) disease comprising the step of administering to a subject in need thereof an effective amount of polynucleotides, cells, and/or vector(s), as contemplated herein and/or produced by a process as contemplated herein.

Possible indications for administration of the composition(s) of the exemplary polynucleotides and/or modified cells are cancerous diseases, including tumorous diseases, including brain, lymphoma, breast, prostate, lung, and colon cancers or epithelial cancers/carcinomas such as multiple myeloma (MM), breast cancer, colon cancer, prostate cancer, head and neck cancer, skin cancer, cancers of the genito-urinary tract, e.g. ovarian cancer, endometrial cancer, cervix cancer and kidney cancer, lung cancer, gastric cancer, cancer of the small intestine, liver cancer, pancreas cancer, gall bladder cancer, cancers of the bile duct, esophagus cancer, cancer of the salivary glands and cancer of the thyroid gland, neuroblastoma, medulloblastoma, glioblastoma, hematopoietic malignancies, and so forth. Exemplary indications for administration of the composition(s) of cells are cancerous diseases, including any malignancies that express a particular antigen, for example. In addition, it includes malignancies that aberrantly express other tumor antigens and those may also be targeted. The administration of the composition(s) of the disclosure is useful for all stages and types of cancer, including for minimal residual disease, early cancer, advanced cancer, and/or metastatic cancer and/or refractory cancer, for example.

The disclosure further encompasses co-administration protocols with other compounds, e.g. bispecific antibody constructs, targeted toxins or other compounds, which act via immune cells. The clinical regimen for co-administration of the inventive compound(s) may encompass co-administration at the same time, before and/or after the administration of the other component. Particular combination therapies include chemotherapy, radiation, surgery, hormone therapy, or other types of immunotherapy.

Embodiments relate to a kit comprising one or more polynucleotides as described herein, a vector as described herein and/or a host cell(s) as described herein. It is also contemplated that the kit of this disclosure comprises a pharmaceutical composition as described herein, either alone or in combination with further medicaments to be administered to an individual in need of medical treatment or intervention.

In ex vivo embodiments, the cells that have been modified with the construct(s) may be then grown in culture under selective conditions and cells that are selected as having the construct may then be expanded and further analyzed, using, for example; the polymerase chain reaction for determining the presence of the construct(s) in the host cells. Once the modified host cells have been identified, they may then be used as planned, e.g., expanded in culture or introduced into a host organism.

Depending upon the nature of the cells, the cells may be introduced into a host organism, e.g., a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

The polynucleotide introduction need not result in integration in every case. In some situations, transient maintenance of the polynucleotide introduced may be sufficient. In this way, one could have a short term effect, where cells could be introduced into the host at a local site or introduced and then turned on after a predetermined time, for example, after the cells have been able to home to a particular site.

The cells may be administered as desired. Depending upon the response desired, the manner of administration, the life of the cells, the number of cells present, various protocols may be employed. The number of administrations will depend upon the factors described above at least in part.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells that could be administered to the population at large, each patient would be monitored for the proper dosage for the individual, and such practices of monitoring a patient are routine in the art.

IV. Cells Generally

In particular embodiments, cells are manipulated ex vivo or in vivo to harbor a polynucleotide that expresses a fusion protein of a CD47-binding entity and an FC receptor-binding entity.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, a "host cell" can refer to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells that do not contain a recombinantly introduced nucleic acid.

In certain embodiments, it is contemplated that RNAs or DNAs or proteinaceous sequences may be co-expressed with other selected RNAs, DNAs, or proteinaceous sequences in the same host cell. Co-expression may be achieved by co-transfecting the host cell with two or more distinct recombinant vectors. Alternatively, a single recombinant vector may be constructed to include multiple distinct coding regions for DNAs or RNAs, which could then be expressed in host cells transfected with the single vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells used in the disclosure are eukaryotic, including mammalian, although prokaryotic cells may be employed for manipulation in recombinant engineering of vectors or DNA to integrate into the vectors. The cells are particularly human, but can be associated with any animal of interest, particularly domesticated animals, such as equine, bovine, murine, ovine, canine, feline, etc. for use in their respective animal.

The cells can be autologous cells, syngeneic cells, allogenic cells and even in some cases, xenogeneic cells, such as in relation to the individual that is receiving the cells. The cells may be modified by changing the major histocompatibility complex ("MHC") profile, by inactivating $\beta_2$-microglobulin to prevent the formation of functional Class I MHC molecules, inactivation of Class II molecules, providing for expression of one or more MHC molecules, enhancing or inactivating cytotoxic capabilities by enhancing or inhibiting the expression of genes associated with the cytotoxic activity, or the like.

Expression vectors that encode the fusion protein can be introduced into the cells as one or more DNA molecules or constructs, where there may be at least one marker that will allow for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the cells by any convenient means. The constructs may be integrated and packaged into non-replicating, defective viral genomes like Adenovirus, Adeno-associated virus (AAV), or Herpes simplex virus (HSV) or others, including retroviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In many situations one may wish to be able to kill the modified cells, where one wishes to terminate the treatment, the cells become neoplastic, in research where the absence of the cells after their presence is of interest, or other event. For this purpose one can provide for the expression of certain gene products in which one can kill the modified cells under controlled conditions. Suicide gene products, such as caspase 9, are examples of such products.

By way of illustration, cancer patients or patients susceptible to cancer or suspected of having cancer may be treated as follows. Cells modified as described herein may be administered to the patient and retained for extended periods of time. The individual may receive one or more administrations of the cells. The cell(s) would be modified and provided to the individual in need thereof.

V. Combination Therapy

In some cases, the composition that comprises the polynucleotide that encodes a fusion protein comprising a CD47-binding entity and a FC receptor-binding entity also comprises an additional cancer therapy. The additional cancer therapy may be a part of the composition, or may be separate from the composition. When the additional cancer therapy is separate from the CD47-binding fusion protein, it may be provided before, during, and/or after the delivery of the CD47-binding fusion protein. In some cases the individual has become resistant to the additional therapy, whereas in other cases the additional cancer therapy provides an additive or synergistic effect when used with the CD47-binding fusion protein. The CD47-binding fusion protein and the additional cancer therapy may be provided to the individual at different times, dosing regimens, and/or delivery routes.

In either case of the additional cancer therapy being a part of the same composition as the CD47-binding fusion protein or a different composition, the additional cancer therapy may be a drug, surgery, radiation, immunotherapy, hormone therapy, or a combination thereof. The additional cancer therapy may be in the form of polynucleotide(s), peptide(s), oligonucleotide(s), protein(s), and/or small molecules, for example. The additional cancer therapy may comprise one or more antibodies, and the antibody may be of any kind, including scFvs, monoclonal antibodies, bispecific antibodies, polyclonal antibodies, and so forth; in such cases the antibody may in its entirety be the therapy, or the antibody may be an element of another composition (such as present on a cell).

In some cases, the combination therapy is gene therapy, such as delivery of a polynucleotide that encodes a therapeutic gene product (therapeutic either directly or indirectly). In such cases, the polynucleotide that encodes the therapeutic gene product may or may not be the same molecule as the polynucleotide that encodes the fusion protein comprising a CD47-binding entity and a FC receptor-binding entity. When the polynucleotide that encodes the therapeutic gene product is on the same molecule as the polynucleotide that encodes the fusion protein, each may or may not be regulated by the same regulatory sequence(s). The polynucleotide may encode one or more cytokines, one or more chemokines, especially of the CXC, CC, CX3C, or XC families, one or more costimulatory molecules, and/or one or more polynucleotides that edit the genome or silence gene expression of cancer cells and/or other cells in the tumor microenvironment (such as those that comprise shRNAs, zinc finger nucleases, TALENs, and/or CRIPR/Cas9 genes that silence or knock out negative regulators (for example, CTLA4, PD1, PD-L1, TIM3, LAG3, IDO, or a combination thereof)). Examples of cytokines include at least IL2, IL7, IL12, IL15, and/or IL21. Examples of costimulatory molecules include at least CD70, CD80, CD86, CD134L, CD137L, other tumor necrosis factor (TNF) superfamily members, and combinations thereof.

In some cases, a polynucleotide is incorporated into a cell, and any cell may comprise at least part of an additional cancer therapy composition.

In cases wherein the additional cancer therapy comprises chemotherapy, all classes of chemotherapeutic agents including alkylating agents, antimetabalites, plant alkaloids, antibiotics, hormonal agents, and/or miscellaneous anticancer drugs may be employed. Specific agents include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, fuldarabine, navelbine, farnesyl-protein tansferase inhibitors, transplatinum, 5-fluorouracil, vincristin, and vinblastin, or any analog or derivative variant of the foregoing and also combinations thereof.

VI. Polynucleotides Generally

The present disclosure encompasses a composition comprising a polynucleotide encoding a fusion protein comprising a CD47-binding entity and a FC receptor-binding entity. The nucleic acid molecule is a recombinant nucleic acid molecule, in particular aspects and may be synthetic. It may comprise DNA, RNA as well as PNA (peptide nucleic acid) and it may be a hybrid thereof.

Furthermore, it is envisaged for further purposes that nucleic acid molecules may contain, for example, thioester bonds and/or nucleotide analogues. The modifications may be useful for the stabilization of the nucleic acid molecule against endo- and/or exonucleases in the cell. The nucleic acid molecules may be transcribed by an appropriate vector comprising a chimeric gene that allows for the transcription of said nucleic acid molecule in the cell. In this respect, it is also to be understood that such polynucleotides can be used for "gene targeting" or "gene therapeutic" approaches. In another embodiment the nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches.

The nucleic acid molecule(s) may be a recombinantly-produced chimeric nucleic acid molecule comprising any of the aforementioned nucleic acid molecules either alone or in combination. In specific aspects, the polynucleotide molecule is part of a vector.

The present disclosure therefore also relates to a composition comprising a vector comprising the nucleic acid molecule described in the present disclosure.

Many suitable vectors are known to those skilled in molecular biology, the choice of which would depend on the function desired and include plasmids, cosmids, viruses, bacteriophages and other vectors used conventionally in genetic engineering. Methods that are well known to those skilled in the art can be used to construct various plasmids and vectors; see, for example, the techniques described in Sambrook et al. (1989) and Ausubel, Current Protocols in Molecular Biology, Green Publishing Associates and Wiley Interscience, N.Y. (1989), (1994). Alternatively, the polynucleotides and vectors of the disclosure can be reconstituted into liposomes for delivery to target cells. A cloning vector may be used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

In specific embodiments, there is a vector that comprises a nucleic acid sequence that is a regulatory sequence operably linked to the nucleic acid sequence encoding a fusion protein defined herein. Such regulatory sequences (control elements) are known to the artisan and may include a promoter, a splice cassette, translation initiation codon, translation and insertion site for introducing an insert into the vector. In specific embodiments, the nucleic acid molecule is operatively linked to said expression control sequences allowing expression in eukaryotic or prokaryotic cells.

It is envisaged that a vector is an expression vector comprising the nucleic acid molecule encoding a fusion protein as defined herein. In specific aspects, the vector is a viral vector, such as a lentiviral vector. Lentiviral vectors are commercially available, including from Clontech (Mountain View, Calif.) or GeneCopoeia (Rockville, Md.), for example.

The term "regulatory sequence" refers to DNA sequences that are necessary to effect the expression of coding sequences to which they are ligated. The nature of such control sequences differs depending upon the host organism. In prokaryotes, control sequences generally include promoters, ribosomal binding sites, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components. In particular embodiments the regulatory sequence is active in tumor cells and/or cells within a tumor microenvironment, such as stroma cells, endothelial cells, immune cells, or a combination thereof.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Thus, the recited vector is an expression vector, in certain embodiments. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the $P_L$, lac, trp or tac promoter in E. coli, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Beside elements that are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pEF-Neo, pCDM8, pRc/CMV, pcDNA1, pcDNA3 (Invitrogen), pEF-DHFR and pEF-ADA, (Raum et al. Cancer Immunol Immunother (2001) 50(3), 141-150) or pSPORT1 (GIBCO BRL).

In some embodiments, the expression control sequences are eukaryotic promoter systems in vectors capable of transforming of transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the disclosure may follow. In particular embodiments, one or more encodable sequences are regulated by expression control sequences that are responsive to hypoxic environments.

Additional regulatory elements may include transcriptional as well as translational enhancers. Advantageously, the above-described vectors of the disclosure comprises a selectable and/or scorable marker. Selectable marker genes useful for the selection of transformed cells are well known to those skilled in the art.

As described above, the recited polynucleotide can be used in a cell, alone, or as part of a vector to express the encoded polypeptide in cells. The nucleic acid molecules or vectors containing the DNA sequence(s) encoding any one of the specific fusion protein constructs is introduced into the cells that in turn produce the polypeptide of interest. The recited nucleic acid molecules and vectors may be designed for direct introduction or for introduction via liposomes, or viral vectors (e.g., adenoviral, retroviral) into a cell.

In accordance with the above, the present disclosure relates to methods to derive vectors, particularly plasmids, cosmids, viruses and bacteriophages used conventionally in genetic engineering that comprise a nucleic acid molecule encoding the polypeptide sequence of a fusion protein encompassed herein. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the recited polynucleotides or vector into targeted cell populations. Methods which are well known to those skilled in the art can be used to construct recombinant vectors; see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the disclosure can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

VII. Vectors Generally

The polynucleotide molecules of the present disclosure may be expressed from an expression vector. Recombinant techniques to generate such expression vectors are well known in the art.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

A. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5 prime non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

In particular embodiments, the expression of a secretable engager molecule polypeptide is modulated. The expression may be modulated in a variety of ways, although in specific embodiments one or more regulatory sequences direct expression of a polynucleotide that encodes an engager polypeptide in a spatial and/or temporal manner. In some cases, the expression is modulated to increase expression of a polynucleotide that encodes an engager polypeptide, such that there is a corresponding increase in the level of engager polypeptide in the immune cell or secreted therefrom. In some cases the expression is modulated to decrease expression of a polynucleotide that encodes a CD47-binding fusion protein molecule, such that there is a corresponding decrease in the level of engager polypeptide in the immune cell or secreted therefrom. Situations where the expression may be desired to be decreased include those where the engager is undesired or no longer desired, for example in normal tissue. The modulation of expression may be compared to the level of expression in the absence of the particular regulatory sequence or factor(s) that regulates it.

In certain embodiments, the expression of a CD47-binding fusion protein polypeptide is modulated upon exposure of a corresponding regulatory sequence to one or more factors. In specific embodiments, the expression is modulated upon exposure to tumor-associated factors. Illustrative examples of tumor-associated factors include factors present in hypoxic tissue. In some embodiments, the factors are cytokines and/or chemokines. For example, hypoxia induces the expression of HIF-1α, a transcription factor that could induce engager expression that is under the control of a hypoxia response element (HRE). Hypoxia could also stabilize engager molecules that contain an oxygen-dependent degradation domain (ODDD). Another example of a substance, which is produced by tumor cells and could regulate engager gene expression, is lactic acid. A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments, the use of internal ribosome entry sites (IRES) elements are used to create multigene, or polycistronic, messages, and these may be used in the embodiments. In certain embodiments 2A sequences are used to create multigene messages, and these may be used in the embodiments.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

B. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with □ galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

C. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present disclosure may be a viral vector that encodes one or more CARs of the disclosure. Non-limiting examples of virus vectors that may be used to deliver a nucleic acid of the present disclosure are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the cells of the present disclosure as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding the desired sequence) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

In particular embodiments, the retrovirus comprises an envelope proteins (env) protein that determines the range of host cells which can ultimately be infected and transformed by recombinant retroviruses generated from the cell lines. Illustrative examples of retroviral-derived env genes which can be employed in the invention include, but are not limited to: VSV-G, MLV envelopes, 10A1 envelope, BAEV, FeLV-B, RD114, SSAV, Ebola, Sendai, FPV (Fowl plague virus), gp41 and gp120, and influenza virus envelopes.

In one embodiment, the invention provides retrovirus pseudotyped with the VSV-G glycoprotein.

4. Other Viral Vectors

Other viral vectors may be employed as vaccine constructs in the present disclosure. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

5. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

D. Vector Delivery and Cell Transformation

Suitable methods for nucleic acid delivery for transfection or transformation of cells are known to one of ordinary skill in the art. Such methods include, but are not limited to, direct delivery of DNA such as by ex vivo transfection, by injection, and so forth. Through the application of techniques known in the art, cells may be stably or transiently transformed.

E. Ex Vivo Transformation

Methods for transfecting eukaryotic cells and tissues removed from an organism in an ex vivo setting are known to those of skill in the art. Thus, it is contemplated that cells or tissues may be removed and transfected ex vivo using nucleic acids of the present disclosure. In particular aspects, the transplanted cells or tissues may be placed into an organism. In preferred facets, a nucleic acid is expressed in the transplanted cells.

VIII. Pharmaceutical Compositions

In accordance with this disclosure, the term "pharmaceutical composition" relates to a composition for administration to an individual. In specific aspects of the disclosure, the pharmaceutical composition comprises a polynucleotide that encodes a fusion protein comprising a CD47-binding entity and a FC receptor-binding entity, and, in some cases, cells that harbor such a polynucleotide. In a particular embodiment, the pharmaceutical composition comprises a composition for parenteral, transdermal, intraluminal, intra-arterial, intrathecal or intravenous administration or for direct injection into a cancer. It is in particular envisaged that said pharmaceutical composition is administered to the individual via infusion or injection. Administration of the suitable compositions may be effected by different ways, e.g., by intravenous, subcutaneous, intraperitoneal, intramuscular, topical or intradermal administration.

The pharmaceutical composition of the present disclosure may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well-known conventional methods. These pharmaceutical compositions can be administered to the subject at a suitable dose.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

The compositions of the disclosure may be administered locally, although in alternative embodiments it is administered systemically, so long as it does not elicit harmful side effects. Administration will generally be parenteral, e.g., intravenous; DNA may also be administered directly to the target site, e.g., by biolistic delivery to an internal or external target site or by catheter to a site in an artery. In a preferred embodiment, the pharmaceutical composition is administered subcutaneously and in an even more preferred embodiment intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present disclosure might comprise proteinaceous carriers, like, e.g., serum albumin or immunoglobulin, preferably of human origin. It is envisaged that the pharmaceutical composition of the disclosure might comprise, in addition to the constructs or nucleic acid molecules or vectors encoding the same (as described in this disclosure), further biologically active agents, depending on the intended use of the pharmaceutical composition.

IX. Kits of the Disclosure

Any of the compositions described herein, or components thereof, may be comprised in a kit. In a non-limiting example, polynucleotides, cells or reagents to manipulate or generate certain polynucleotides, proteins, and/or peptides may be comprised in a kit. Such a kit may or may not have one or more reagents for manipulation of cells. Such reagents include small molecules, proteins, nucleic acids, antibodies, buffers, primers, nucleotides, salts, and/or a combination thereof, for example. In particular embodiments, a polynucleotide that encodes a fusion protein that comprises a CD47-binding entity and a FC receptor-binding entity, or each component separately, or primers suitable for amplifying either entity, may be provided in a kit. In some cases, cells for harboring such a polynucleotide(s) may be provided in a kit, and/or an apparatus to obtain cells from an individual may be provided in the kit.

Polynucleotides that encode one or more cytokines, or cytokines themselves, may also be included in the kit. Proteins, such as cytokines or antibodies, including agonistic monoclonal antibodies, may be included in the kit, and/or cancer drugs may be included.

In particular aspects, the kit comprises the polynucleotide and/or cell therapy of the disclosure and also another cancer therapy. In some cases, the kit, in addition to the polynucleotide and/or cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

The kits may comprise suitably aliquoted compositions of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also may generally contain a second, third or other additional container into which the additional components may be separately placed. However, various combinations of components may be comprised in a vial. The kits of the present invention also will typically include a means for containing the composition and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1B:
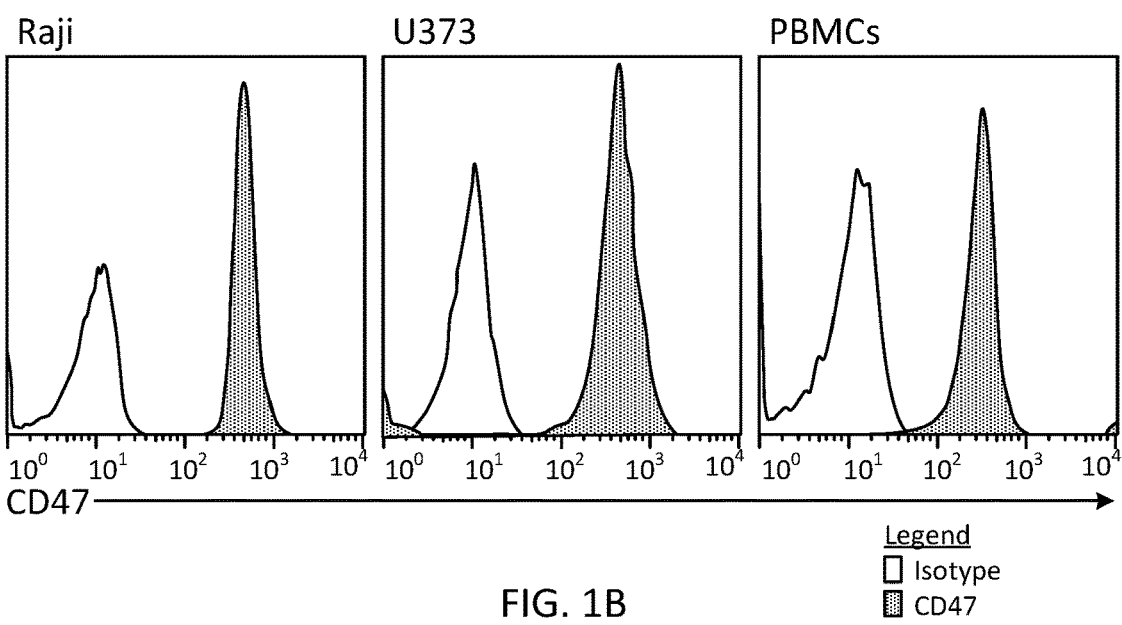
Figure 1C:
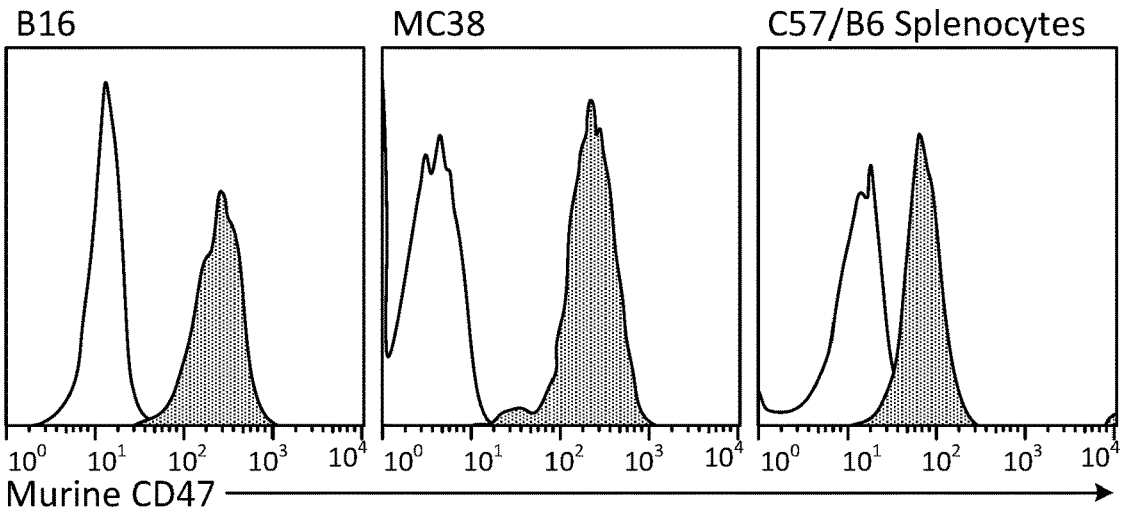
Figure 2A:
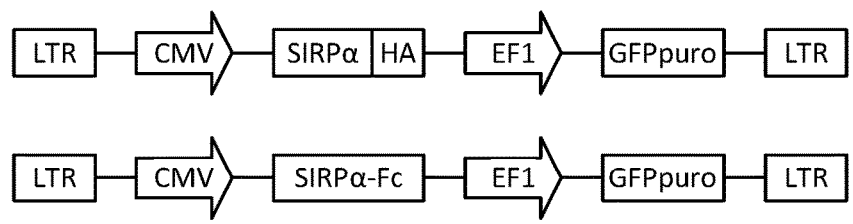
FIGS. 2A-2D: Demonstration that a variety of cell lines can be transduced to express either SIRPα or SIRPα-Fc.
Figure 2B:
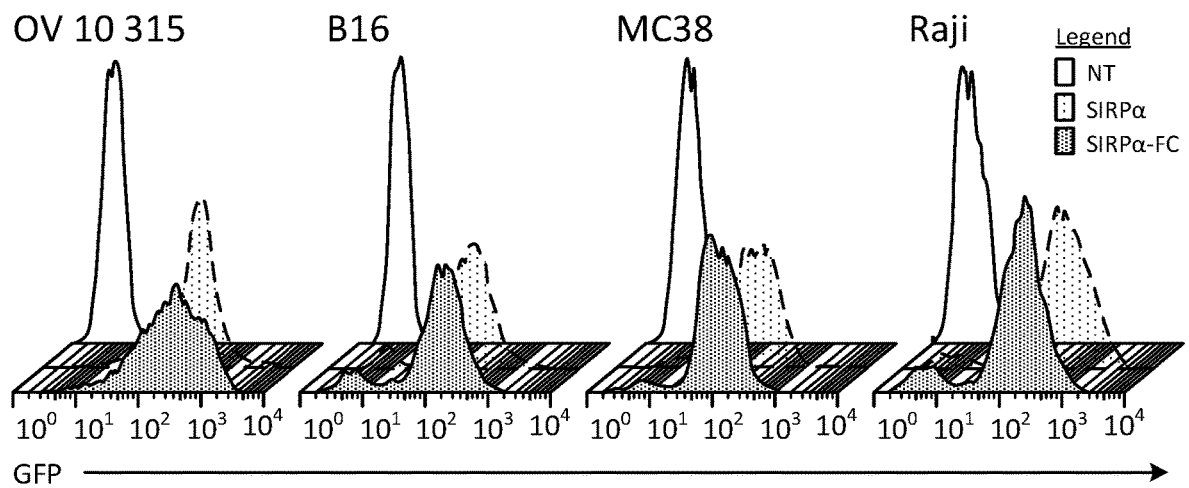
Figures 2C, 2D:
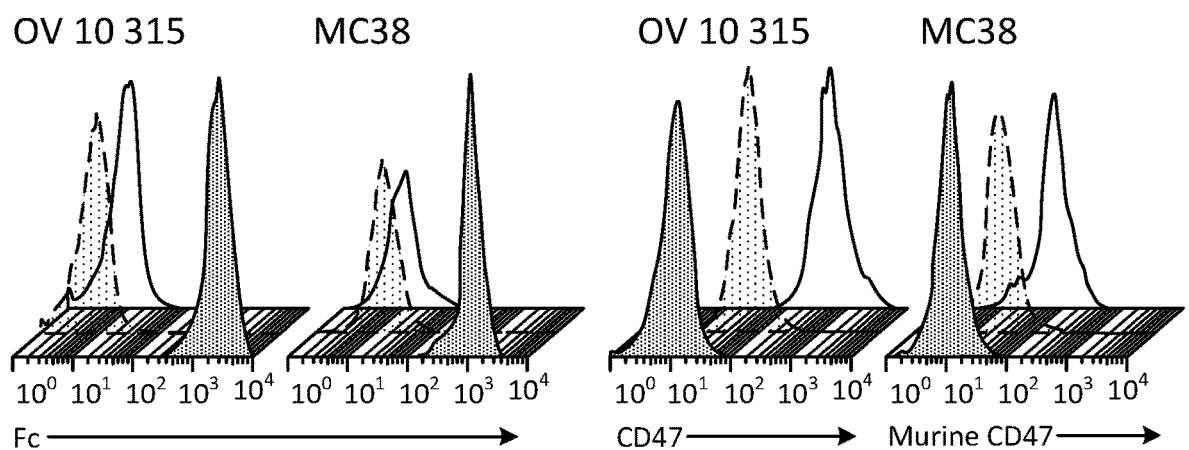

Cancer Cells Express CD47 and can be Genetically Modified with Lentiviral Vectors Encoding SIRPA or SIRP Alpha-FC FIGS. 1A-1C demonstrates expression of CD47 on a panel of human and murine tumor cells by FACS analysis. FIG. 2A shows the scheme of the generated lentiviral vectors that either encode SIRPα or SIRPα-Fc and GFP. In the generated lentiviral vectors we used the derivative of the SIRPα ectodomain CV1. The generated lentiviral vectors were used to transduce tumor cells. Judging by FACS analysis for GFP expression, greater than 90% of tumor cells were transduced (FIG. 2B). Only tumor cells that were transduced with SIRPα-Fc were stained with a FC antibody demonstrating that full length SIRPα-Fc was expressed (FIG. 2C). The ability of CD47 antibodies to detect CD47 on the cell surface of cancer cells was diminished in cancer cells that expressed SIRPα and SIRPα-Fc, indicating that SIRPα and SIRPα-Fc binds to CD47 (FIG. 2D).

Figure 3:
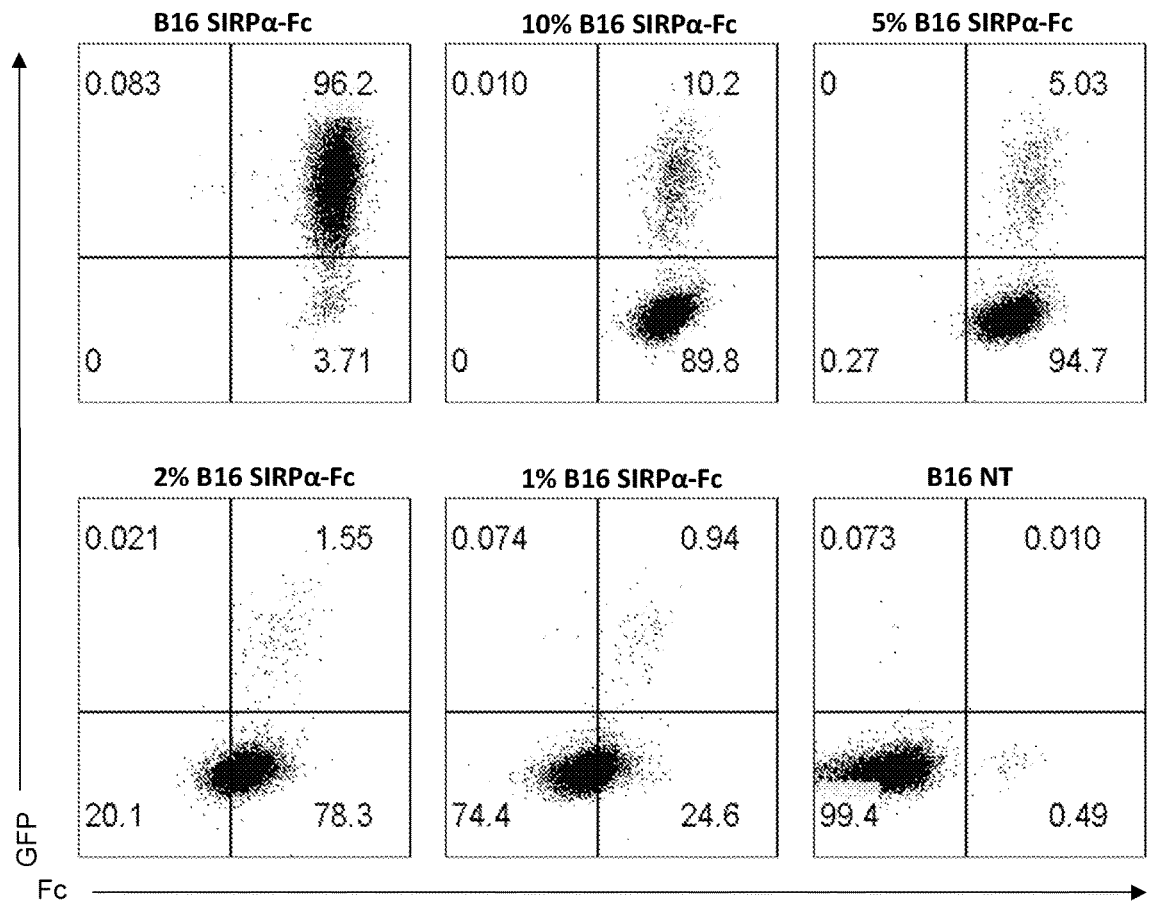
FIG. 3: Demonstration that SIRP α-Fc-transduced cells secrete SIRPα-Fc molecules, which can bind to non-transduced cells. B16 cells transduced with pCDH.CMV.SIRPα-Fc.EF1.GFPpuro (B16-SIRPα-Fc) were co-cultured for 24 hours with NT B16 cells at various ratios (100%, 10%, 5%, 2%, 1%, 0%). Cells were harvested and B16-SIRPα-Fc cells were detected by FACS analysis for GFP, and cell surface bound SIRPα-Fc was detected by FACS analysis using Alexa-Fluor 647 CH2CH3 antibody (Fc).

To demonstrate that tumor cells secrete SIRPα-Fc expressing B16 tumor cells were co-cultured for 24 hours with non-transduced B16 cells at various ratios (100%, 10%, 5%, 2%, 1%, 0%). While non-transduced B16 tumor cells, which were cultured by themselves, were negative for Fc, 78% of non-transduced B16 tumor cells were positive in cocultures with only 2% transduced B16 cells (FIG. 3). This demonstrates that transduced tumor cells secrete functional SIRPα-Fc, which binds to CD47 present on non-transduced tumor cells.

Example 2

Figure 4:
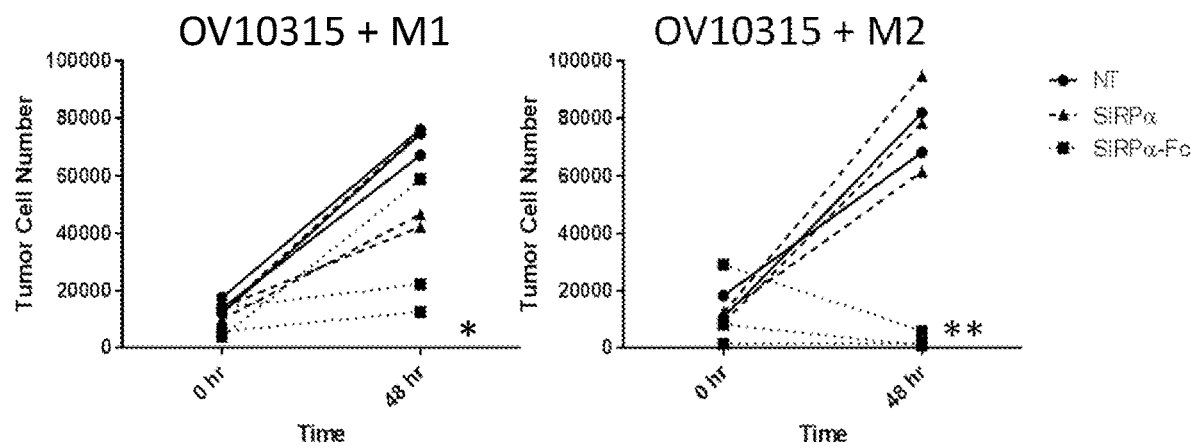
FIG. 4: Demonstration that human M1 and M2 macrophages kill SIRPα-Fc-expressing OV10 315 cells but not NT or SIRPα-expressing cells. Macrophages were generated from monocytes obtained by CD14+ MACS selection from healthy donor peripheral blood mononuclear cells (PBMCs). Monocytes were cultured with 100 ng/mL M-CSF for 5 days and then polarized to M1 macrophages with 100 ng/mL LPS and 20 ng/mL IFNγ or to M2 macrophages with 20 ng/mL IL-4 for 48 hours. Macrophage were co-cultured with OV10 315 NT, OV10 315-SIRPα or OV10 315-SIRPα-Fc cells at 5:1 effector to target ratio. Cells were harvested for FACS analysis the day of co-culture (0 hr) and 48 hours later (48 hrs). Cells were stained with anti-CD33 PE, to distinguish the macrophage population, and 7AAD to exclude dead cells. Fluorescent counting beads (Life Technologies) were used to calculate total number of macrophages (CD33+) and OV10 315 tumor cells (CD33−). * Indicates p<0.05 for OV10315 NT vs. OV10 315 SIRPα-Fc with two-way ANOVA. ** Indicates p<0.05 for OV10315 NT vs. OV10 315 SIRPα-Fc and OV10 315 SIRPα vs OV10 315 SIRPα-Fc with two-way ANOVA.

SIRP Alpha-FC Expressing Tumor Cells are Phagocytosed (and Killed) by Macrophages Having established that tumor cells can be genetically modified to express SIRPα and SIRPα-Fc, we next set out to determine if M1 and/or M2 macrophages can phagocytose and kill tumor cells. M1 and M2 macrophages were generated by standard methods from PBMC-derived monocytes. M1 and M2 macrophages were co-cultured with OV10 315 NT, OV10 315-SIRPα or OV10 315-SIRPα-Fc cells at 5:1 effector to target ratio. After 48 hours the presence of viable tumor cells was determined by FACS analysis. M2 macrophages effectively killed OV10 315-SIRPα-Fc in contrast to OV10 315 NT and OV10 315-SIRPα, demonstrating that SIRPα-Fc sensitizes tumor cells to M2 macrophage-mediated killing (FIG. 4). M1 macrophages had significant in 2 out of 3 donors. Since M2 macrophages are the predominant macrophages within tumor, these results highlight the impact of our invention.

Example 3

SIRP Alpha-FC Expressing Tumor Cells have Reduced Tumorgenicity in Preclinical Tumor Models Having demonstrated that SIRPα-FC expressing tumor cells are killed by macrophages, we next determined if these tumor cells have reduced tumorigenicity using three animal models (Raji, B16, MC38).

Raji Model (Lymphoma):

NSG mice were injected i.v. with Raij, Raij-SIRPα, or Raij-SIRPα-FC cells (n=5 per group). Raij or Raij-SIRPα injected mice started to lose weight (wt) and needed to be euthanized by day 21, 3/5 Raij-SIRPα-FC injected mice consistently gained weight and did not develop tumors at all; 2/5 Raij-SIRPα-FC injected mice, developed tumors, and needed to be euthanized on day 40 and day 47 (FIG. 5A).

B16 Model (Melanoma):

C57BL/6 mice were injected s.c. with B16, B16-SIRPα, or B16-SIRPα-FC cells (n=5 per group). Tumor size was monitored by caliper measurements. While there was no difference in tumor growth, the tumorigenicity of B16-SIRPα-FC was greatly reduced leading to a survival advantage (FIG. 5A).

MC38 Model (Colon Cancer):

C57BL/6 mice were injected s.c. with MC38, MC38-SIRPα, or MC38-SIRPα-FC cells (n=4-5 per group). Tumor size was monitored by caliper measurements. 4/4 MC38 mice developed tumors and eventually had to be euthanized while only 1/5 MC38-SIRPα and 1/5 MC38-SIRPα-FC mice developed tumors at later time point in comparison to unmodified MC38 cells (FIG. 5B).

Figure 5C:
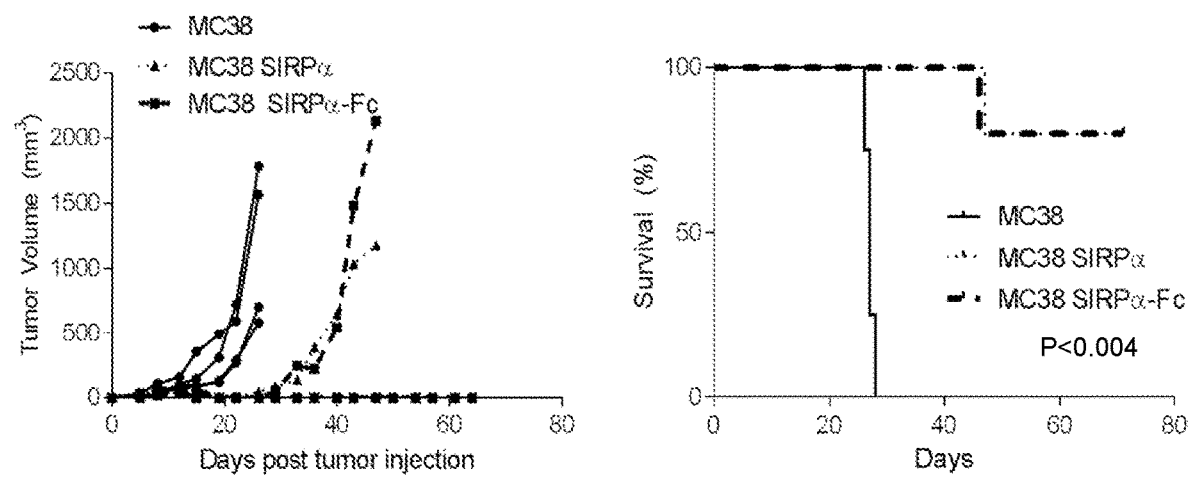

Thus in all three animal models, SIRPα-FC expressing tumor cells had a reduced tumorigenicity with 7/14 animals remaining tumor free and 7/14 animals having delayed tumor growth in comparison to controls (FIG. 5C).

Example 4

Construction and Functional Analysis of Vaccina Viruses Encoding SIRP Alpha or SIRP Alpha-FC Having shown the feasibility of using lentiviruses to genetically modify tumor cells to express SIRPα or SIRPα-Fc we next wanted to demonstrate that it is possible to generate oncolytic viruses expressing SIRPα or SIRPα-Fc to transduce tumor cells. We generated VV expressing SIRPα or SIRPα-Fc using standard methods, and for VV generation used the derivative of the SIRPα ectodomain CV1. In the generated VVs, the SIRPα or SIRPα-FC expression is controlled by the late F17R promoter; the VVs also contain the marker gene yellow fluorescent protein (YFP) to allow for detection (see scheme of shuttle plasmid to generated VV SIRPα-Fc in FIG. 6A). The presence of the SIRPα and SIRPα-Fc in the individual VVs was confirmed by PCR (FIG. 6B).

Figure 7A:
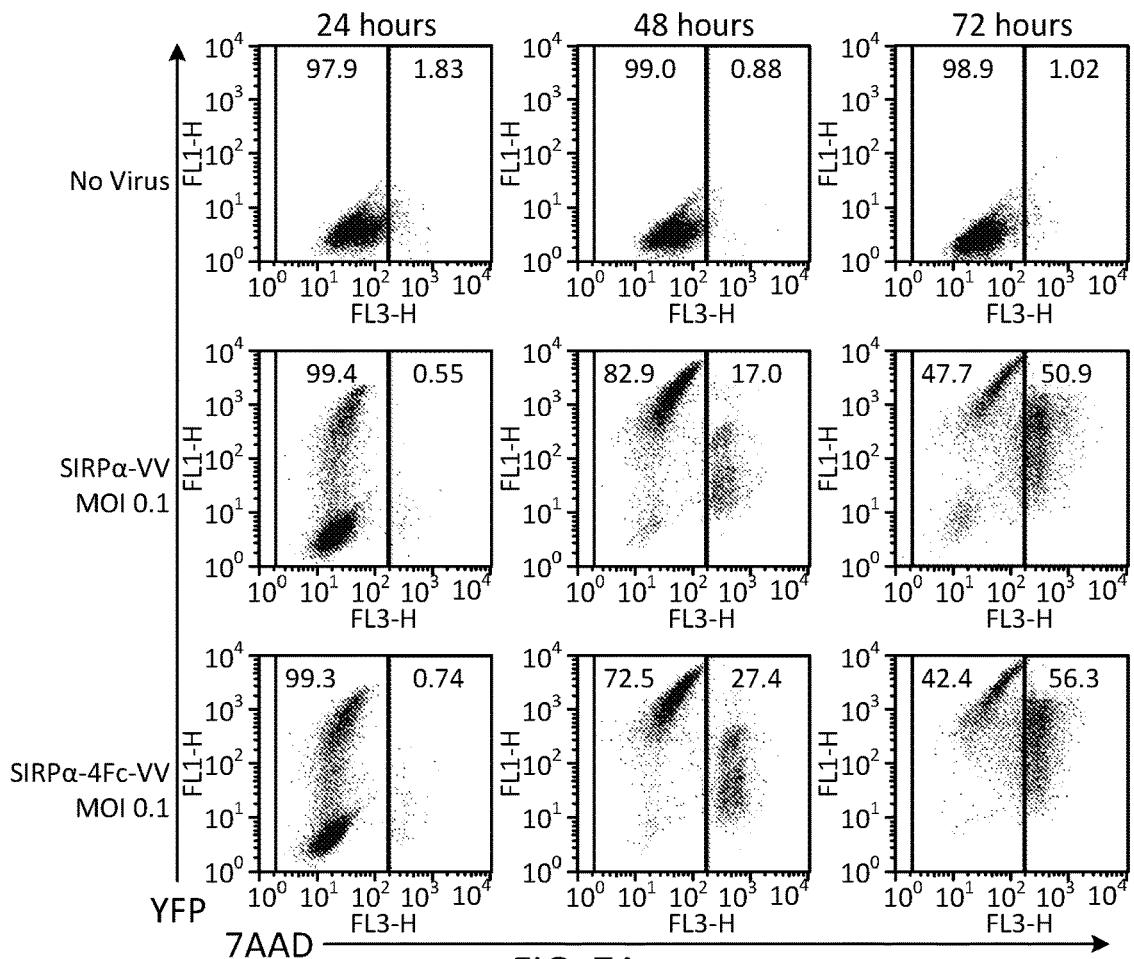
FIGS. 7A-7C: Demonstration that cells infected with SIRPα or SIRPα-Fc express and secrete those molecules.

To determine if tumor cells express functional SIRPα and SIRPα-Fc after SIRPα-VV and SIRPα-Fc-VV infection, OV10 315 tumor cells were infected with indicated SIRPα-VV or SIRPα-Fc-VV at MO1 0.1 and cells were harvested for FACS analysis at 24, 48, and 72 hours post-infection. Both viruses induced tumor cell killing as judged by an increase in YFP positive cells (FIG. 7A). To determine if SIRPα and SIRPα-Fc are expressed, we stained tumor cells with FC antibodies 24 hours and with CD47 antibodies 48 hours post infection. Only tumor cells infected with SIRPα-

Figure 7B:
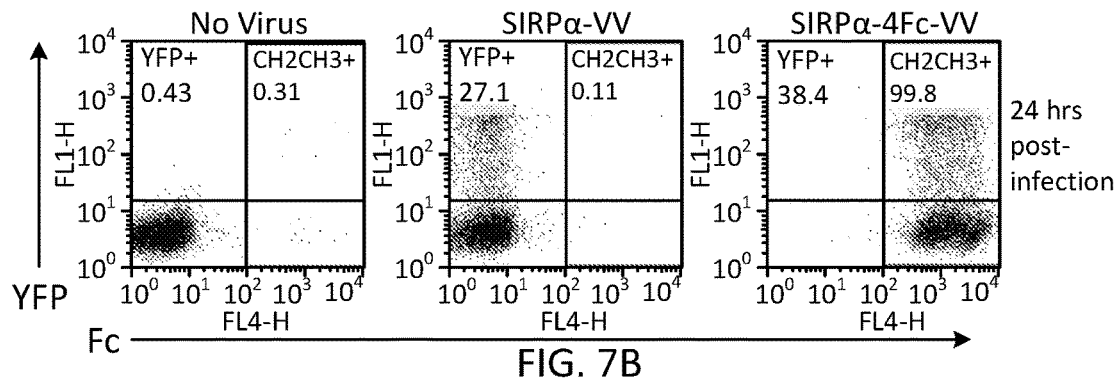
Figure 7C:
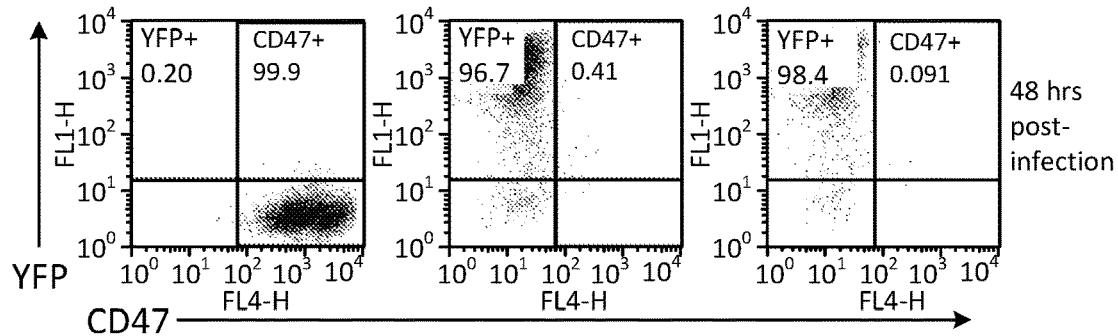

Fc-VV were positive for Fs, indicating expression of functional SIRPα-Fc (FIG. 7B). Of note, all YFP-negative tumor cells were Fc positive, highlighting that infected tumor cells secrete SIRPα-Fc, which then binds to CD47 present on non-infected tumor cells (FIG. 7B). CD47 could not be detected on SIRPα-VV or SIRPα-Fc-VV infected tumor cells in comparison to non-infected tumor cells, demonstrating that SIRPα or SIRPα-Fc-VV effectively block the binding of the CD47 antibody to tumor cells (FIG. 7C).

Figure 8A:
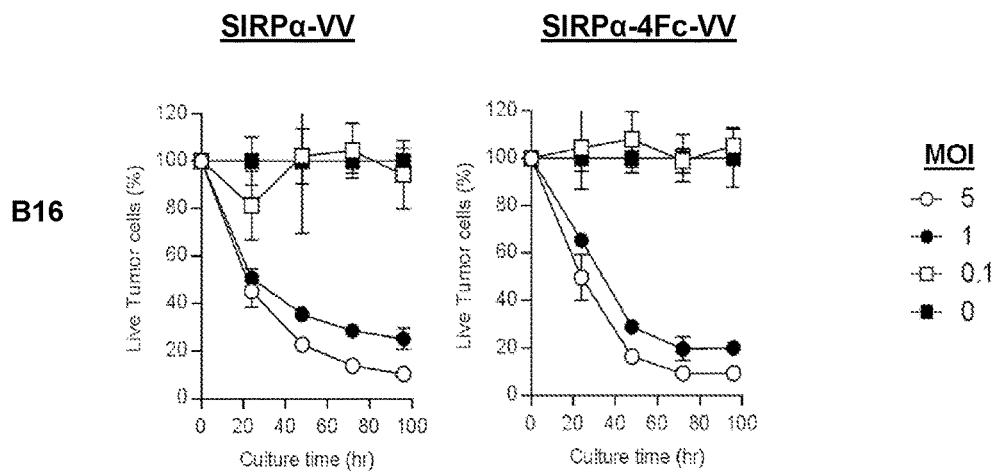
FIGS. 8A-8D: Demonstration SIRPα-VV and SIRPα-Fc-VV have similar oncolytic activity in murine and human cell lines. B16 (FIG. 8A), MC38 (FIG. 8B), F420 (FIG. 8C) and LM7 (FIG. 8D) cells were infected with increasing MOI and cell viability was measured 24, 48, 72, and 96 hrs post infection by absorbance at 492 nm after incubation with MTS reagent for 2 hours. Percent of live tumor cells was calculated by comparing OD492 of each condition with OD492 of non-infected cells. SIRPα-VV and SIRPα-Fc-VV effectively replicated in all tested cell lines and induced significant tumor cell killing, This demonstrates that engineering VVs to express SIRPα or SIRPα-Fc does not interfere with their ability to kill tumor cells.
Figure 8B:
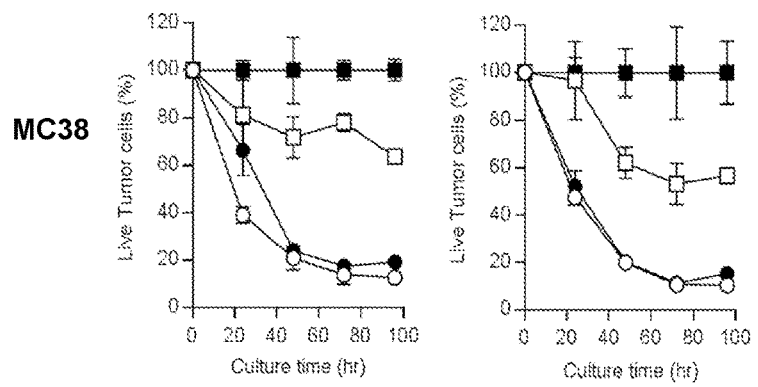
Figure 8C:
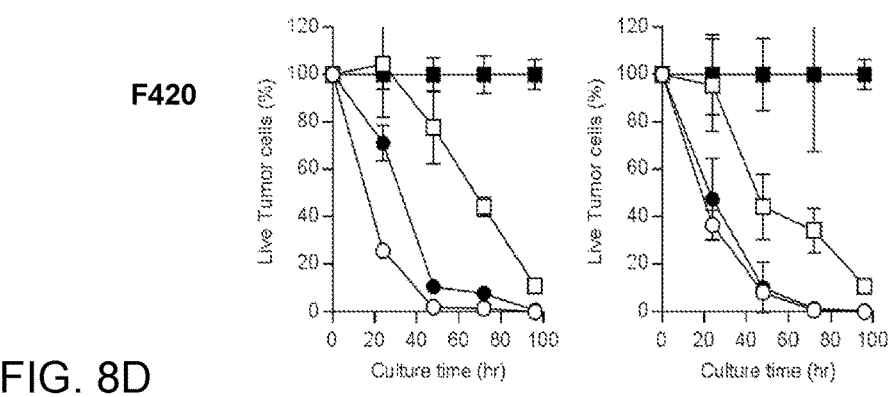
Figure 8D:
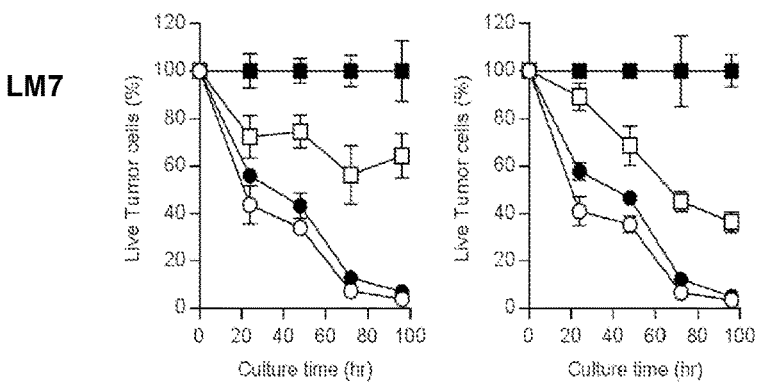

To establish, that SIRPα-VV and SIRPα-Fc-VVs have potent oncolytic activity by themselves murine and human tumor cell lines [B16 (FIG. 8A), MC38 (FIG. 8B), F420 (FIG. 8C) and LM7 (FIG. 8A)] were infected with increasing MOI. Cell viability was measured 24, 48, 72, and 96 hrs post infection using a standard MTS assay. SIRPα-VV and SIRPα-Fc-VV effectively replicated in all tested cell lines and induced tumor cell killing in all four cell lines tested in a MOI dependent manner.

Figure 9:
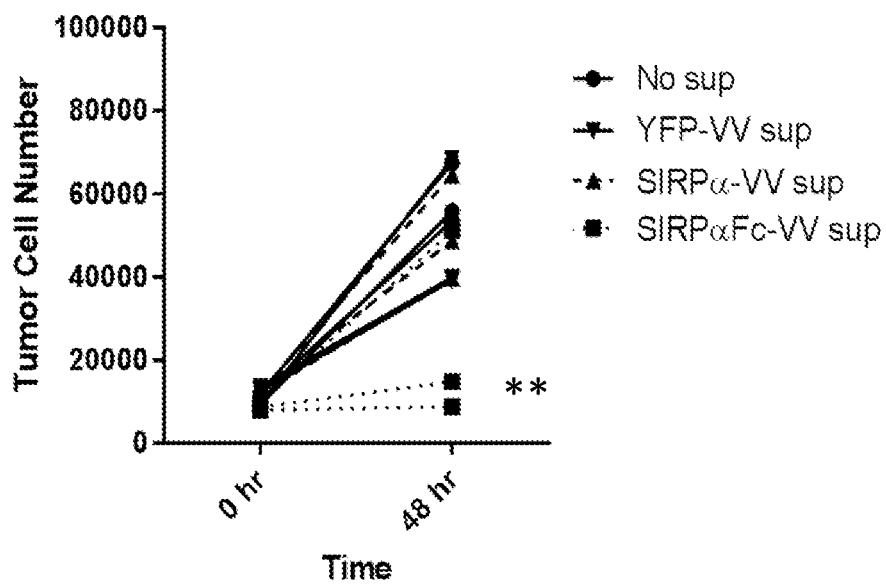
FIG. 9. Demonstration that human M1 and M2 macrophages kill OV10 315 cells incubated with supernatant from SIRPαFc-VV-infected cells, but not YFP-VV or SIRPα-VV-infected cells. Macrophages were generated from monocytes obtained by CD14+ MACS selection from healthy donor peripheral blood mononuclear cells (PBMCs). Monocytes were cultured with 100 ng/mL M-CSF for 5 days and then polarized to M1 macrophages with 100 ng/mL LPS and 20 ng/mL IFNγ or to M2 macrophages with 20 ng/mL IL-4 for 48 hours. Supernatant was collected from OV10 cells (CD47-) infected with MOI 0.1 of either YPP-VV, SIRPα-VV, or SIRPαFc-VV after 48 hours and filtered. Macrophage were co-cultured with OV10 315 cells with either media alone (No sup), or supernatant from YFP-VV-infected cells (YFP-VV sup), SIRPα-VV-infected cells (SIRPα-VV sup), or SIRPαFc-VV-infected cells (SIRPαFC-VV sup) at a 5:1 effector to target ratio. Cells were harvested for FACS analysis the day of co-culture (0 hr) and 48 hours later (48 hrs). Cells were stained with anti-CD33 PE, to distinguish the macrophage population, and 7AAD to exclude dead cells. Fluorescent counting beads (Life Technologies) were used to calculate total number of macrophages (CD33+) and OV10 315 tumor cells (CD33-). p<0.01 for M1+OV10315 No sup vs. M1+OV10 315 with SIRPαFc-VV sup two-way ANOVA. **p<0.0001 for M2+OV10315 No sup vs. M2+OV10 315 with SIRPαFc-VV sup with two-way ANOVA.
Figure 9:
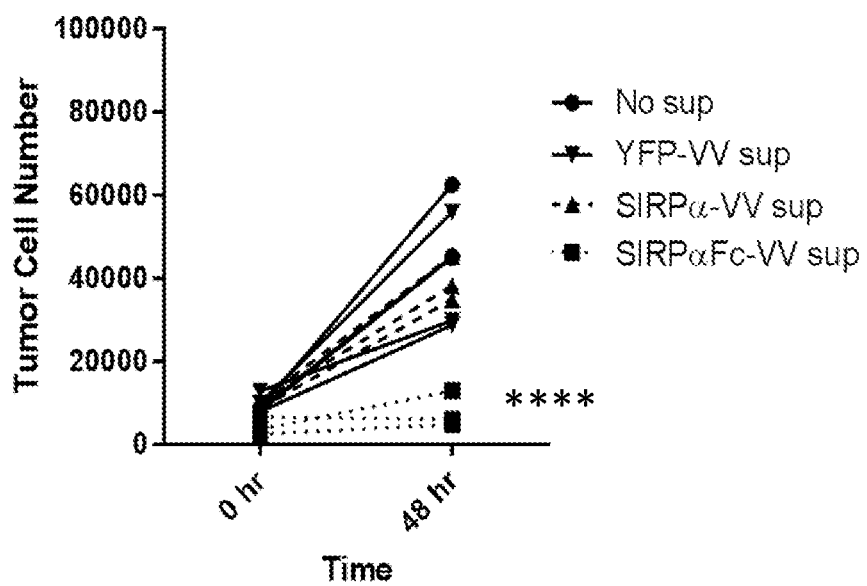
Figure 10:
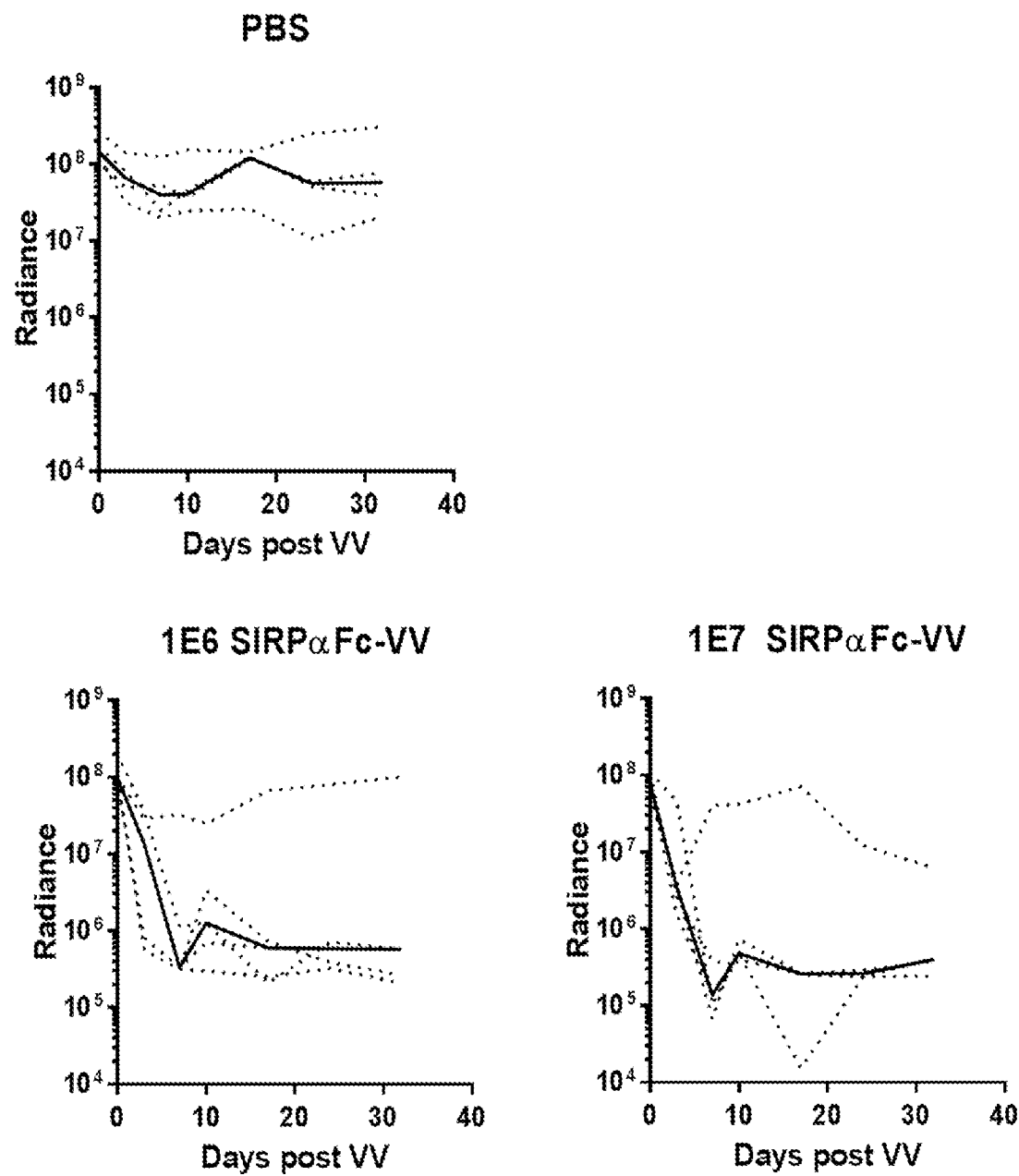
FIG. 10. Demonstration that SIRP αFc-VV has antitumor activity in xenograft model. SCID Beige mice were injected i.p. with 2e6 LM7 GFP ffluc cells (n=4-5/group). 7 days later, mice were injected i.p. with 100 ul of PBS vehicle control, 1×10^6 PFU SIRPαFc-VV, or 1×10^7 PFU SIRPαFc-VV. While tumor bioluminescent signal could still be detected in the PBS group in 4/4 mice, in both groups treated with SIRP αFc-VV, tumor could not be detected in 4/5 mice within 10 days post VV-injection.

In summary, the studies of Example 4 demonstrate that the inventors have generated SIRPα-VV and SIRPα-Fc-VVs, which replicate in tumor cells, and that infected tumor cells express functional SIRPα or SIRPα-Fc. Furthermore, FIG. 9 demonstrates that human M1 and M2 macrophages kill cells incubated with supernatant from SIRPαFc-VV-infected cells and FIG. 10 shows that SIRPαFc-VV has antitumor activity in a xenograft model.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

1. Torre L A, Bray F, Siegel R L, Ferlay J, Lortet-Tieulent J, Jemal A. Global cancer statistics, 2012. CA Cancer J Clin. 2015; 65(2):87-108. doi: 10.3322/caac.21262. PubMed PMID: 25651787.
2. Edwards B K, Noone A M, Mariotto A B, Simard E P, Boscoe F P, Henley S J, et al. Annual Report to the Nation on the status of cancer, 1975-2010, featuring prevalence of comorbidity and impact on survival among persons with lung, colorectal, breast, or prostate cancer. Cancer. 2014; 120(9):1290-314. doi: 10.1002/cncr.28509. PubMed PMID: 24343171; PubMed Central PMCID: PMC3999205.
3. Chanmee T, Ontong P, Konno K, Itano N. Tumor-associated macrophages as major players in the tumor microenvironment. Cancers(Basel). 2014; 6(3):1670-90. doi: cancers6031670 [pii];10.3390/cancers6031670 [doi].
4. Chao M P, Weissman I L, Majeti R. The CD47-SIRPalpha pathway in cancer immune evasion and potential therapeutic implications. CurrOpinImmunol. 2012; 24(2):225-32. doi: S0952-7915(12)00012-X [pii];10.1016/j.coi.2012.01.010 [doi].
5. Weiskopf K, Ring A M, Ho C C, Volkmer J P, Levin A M, Volkmer A K, et al. Engineered SIRPalpha variants as immunotherapeutic adjuvants to anticancer antibodies. Science. 2013; 341(6141):88-91. doi: science.1238856 [pii];10.1126/science.1238856 [doi].
6. Bruhns P. Properties of mouse and human IgG receptors and their contribution to disease models. Blood. 2012; 119(24):5640-9. doi: blood-2012-01-380121 [pii]; 10.1182/blood-2012-01-380121 [doi].
7. Oldenborg P A, Zheleznyak A, Fang Y F, Lagenaur C F, Gresham H D, Lindberg F P. Role of CD47 as a marker of self on red blood cells. Science. 2000; 288(5473):2051-4. doi: 8601 [pii].

What is claimed is:

1. A composition comprising a polynucleotide comprising SEQ ID NO:4 or SEQ ID NO:8 encoding a fusion protein.

2. The composition of claim 1, wherein the polynucleotide further encodes a leader sequence operatively linked to the fusion protein.

3. The composition of claim 1, wherein the polynucleotide further encodes a label or tag that is operatively linked to the fusion protein.

4. The composition of claim 1, wherein the polynucleotide is comprised on a vector.

5. The composition of claim 4, wherein the vector is a viral vector or a non-viral vector.

6. The composition of claim 5, wherein the viral vector is a lentiviral vector, vaccinia viral vector, adenoviral vector, adeno-associated viral vector, Herpes simplex viral vector, myxoma viral vector, reoviral vector, polio viral vector, vesicular stomatitis viral vector, measles viral vector, Newcastle disease viral vector, or retroviral vector.

7. The composition of claim 5, wherein the non-viral vector is a plasmid, nanoparticle, cationic lipid, cationic polymer, lipid polymer, liposome, or combination thereof.

8. The composition of claim 1, wherein the polynucleotide is DNA.

9. The composition of claim 1, wherein the composition comprises an additional cancer therapy.

10. The composition of claim 9, wherein the additional cancer therapy comprises a polynucleotide, peptide, protein, small molecule, or combination thereof.

11. The composition of claim 10, wherein the additional cancer therapy polynucleotide and the polynucleotide that encodes the fusion protein are comprised in a single polynucleotide molecule.

12. The composition of claim 10, wherein the additional cancer therapy polynucleotide and the polynucleotide that encodes the fusion protein are different polynucleotide molecules.

13. The composition of claim 10, wherein the additional cancer therapy polynucleotide encodes a gene product that comprises immune stimulatory function.

14. The composition of claim 13, wherein the gene product that comprises immune stimulatory function comprises one or more cytokines, one or more chemokines, one or more costimulatory molecules, one or more antibody-comprising molecules, one or more gene products that edit the genome or silence gene expression of cancer cells and/or other cells within the tumor microenvironment, or a combination thereof.

15. The composition of claim 14, wherein the cytokines are selected from the group consisting of IL2, IL7, IL12, IL15, IL21, and a combination thereof.

* * * * *